(12) United States Patent
Brown et al.

(10) Patent No.: US 7,999,548 B1
(45) Date of Patent: Aug. 16, 2011

(54) DUAL LOWER EXTREMITY MRI COIL ARRAY WITH SIMULTANEOUSLY INDEPENDENT MRI SIGNAL DETECTION FROM BOTH LEGS

(75) Inventors: Ryan J. Brown, New York, NY (US); Yi Wang, New York, NY (US)

(73) Assignee: Martin R. Prince, New York, NY (US)

( * ) Notice: Subject to any disclaimer, the term of this patent is extended or adjusted under 35 U.S.C. 154(b) by 63 days.

(21) Appl. No.: 12/548,172

(22) Filed: Aug. 26, 2009

Related U.S. Application Data

(60) Provisional application No. 61/092,250, filed on Aug. 27, 2008.

(51) Int. Cl.
*G01V 3/00* (2006.01)
*A61B 5/055* (2006.01)

(52) U.S. Cl. ........ 324/318; 324/309; 324/307; 600/410; 600/422

(58) Field of Classification Search .......... 324/300–322; 600/410–435; 382/128–131
See application file for complete search history.

(56) References Cited

U.S. PATENT DOCUMENTS

| | | | |
|---|---|---|---|
| 2,970,660 A * | 2/1961 | Bodine, Jr. .................. 175/55 |
| 4,825,162 A | 4/1989 | Roemer et al. | |
| 5,430,378 A * | 7/1995 | Jones ............... 324/318 |
| 5,489,847 A | 2/1996 | Nabeshima et al. | |
| 5,500,596 A | 3/1996 | Grist et al. | |
| 5,548,218 A | 8/1996 | Lu | |
| 5,594,337 A * | 1/1997 | Boskamp .............. 324/318 |
| 5,708,361 A | 1/1998 | Wang et al. | |
| 6,137,291 A * | 10/2000 | Szumowski et al. ......... 324/318 |
| 6,300,761 B1 | 10/2001 | Hagen et al. | |
| 6,323,648 B1 | 11/2001 | Belt et al. | |
| 6,438,402 B1 | 8/2002 | Hashoian et al. | |
| 7,336,074 B2 * | 2/2008 | Yang et al. .................. 324/318 |
| 7,348,778 B2 * | 3/2008 | Chu et al. .................... 324/318 |
| 7,701,209 B1 * | 4/2010 | Green .......................... 324/307 |
| 2004/0220469 A1 * | 11/2004 | Jevtic et al. ................. 600/422 |
| 2006/0255803 A1 * | 11/2006 | Chu et al. .................... 324/318 |
| 2007/0273377 A1 * | 11/2007 | Yang et al. .................. 324/318 |

OTHER PUBLICATIONS

Ho KY et al, "Peripheral vascular tree stenoses: evaluation with moving-bed infusion-tracking MR angiography," Radiology 1998;206(3):683-692.
Leifer MC, "Resonant modes of the birdcage", J Magn Reson Imaging 1996;124:51.
Leiner et al., "Use of a three-station phased array coil to improve peripheral contrast-enhanced magnetic resonance angiography," J Magn Reson Imaging 2004; 20:417-425.
Tilley AR, "The measure of man and woman," New York: The Whitney Library of Design, 1993.
Wang Y, et al., "Bolus-chase MR digital subtraction angiography in the lower extremity," Radiology 1998;207(1):263-269.
Wang Y, et al., "Dynamic MR digital subtraction angiography using contrast enhancement, fast data acquisition, and complex subtraction," Magn Res Med 1996;36(4):551-556.

(Continued)

*Primary Examiner* — Melissa Koval
*Assistant Examiner* — Tiffany Fetzner
(74) *Attorney, Agent, or Firm* — Scott E. Kamholz; Peter K. Sollins; Foley Hoag LLP

(57) ABSTRACT

Magnetic resonance imaging of the lower extremities using a coil array having sections of decoupled coil elements that enclose, bilaterally and separately, both legs at the same longitudinal region along the cranial-caudal direction.

28 Claims, 19 Drawing Sheets

OTHER PUBLICATIONS

Wright S, et al., "Theory and application of array coils in MR spectroscopy," NMR Biomed. 1997; 10:394-410.

Zhu H, et al., "High temporal and spatial resolution 4D MRA using spiral data sampling and sliding window reconstruction," Magn Reson Med 2004;52(1):14-18.

* cited by examiner

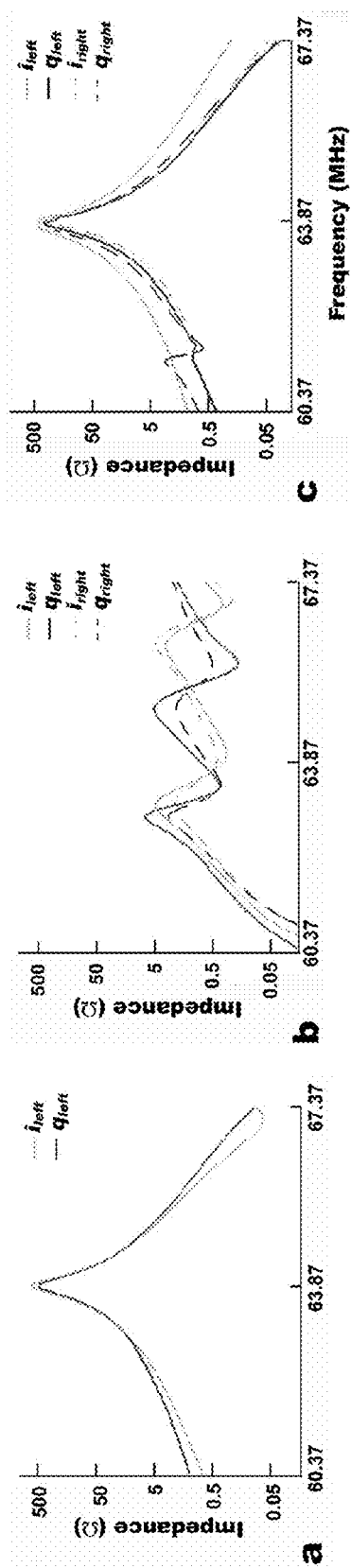

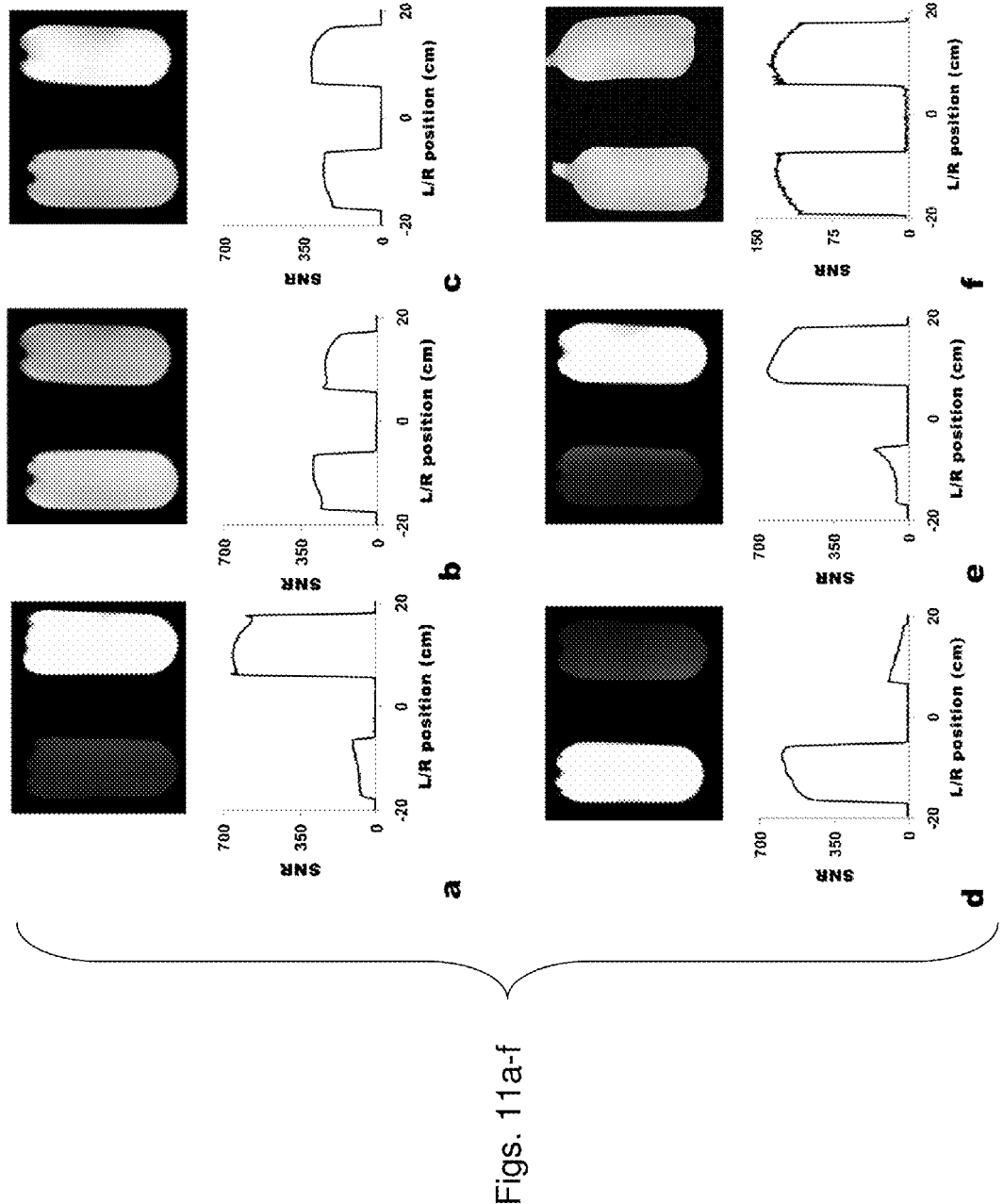
Figs. 11a-f

US 7,999,548 B1

DUAL LOWER EXTREMITY MRI COIL ARRAY WITH SIMULTANEOUSLY INDEPENDENT MRI SIGNAL DETECTION FROM BOTH LEGS

CROSS-REFERENCE TO RELATED APPLICATION

This application claims the benefit of U.S. Provisional Application No. 61/092,250, filed Aug. 27, 2008, which is hereby incorporated herein by reference.

FIELD

The present application relates to magnetic resonance imaging of the lower extremities using a coil array having sections of decoupled coil elements that enclose, bilaterally and separately, both legs at the same longitudinal region along the cranial-caudal direction. As a result of the enclosing coil geometry, the signal detection signal-to-noise ratio is improved compared to that of open coil geometry and geometry singularly enclosing both legs together. This application further relates to magnetic resonance imaging of peripheral vascular disease to better delineate lesions in small distal vessels using sensitive coils.

BACKGROUND

MRI is a widely practiced method for mapping diseases in the lower extremities. Optimizing the design of signal detection coil array for imaging the lower extremities from the pelvis to the feet is a challenging problem become of the long longitudinal extent and the wide variations of anatomical structures. Surface coil arrays described in U.S. Pat. No. 4,825,162 by Roemer et al have been applied to lower extremity coil array designs. These designs typically employ sections of coil elements in an anterior plate or a pair of anterior and posterior plates flexed to the body of the lower extremity and can be grouped into four types of geometries: single enclosure of both legs, anterior flex onto both legs, orthogonal separation between legs, and a pair of anterior-posterior plates. These geometries do not provide the closest possible distance between signal detection coil elements and the anatomic structures of interest.

The geometry of single enclosure of both legs is described in U.S. Pat. Nos. 5,548,218, 6,137,291, and 6,438,402. The flexion of a butterfly surface coil element into a loop enclosing the body is described in U.S. Pat. No. 5,548,218 to provide quadrature signal detection with in-depth and homogeneous sensitivity. U.S. Pat. No. 6,137,291 describes a telescopically tapered array of butterfly coils, which further improves detection SNR because of reduced distance between detection coil elements and anatomic parts. This design is improved by U.S. Pat. No. 6,438,402, which introduces multiple butterfly coils, further reducing the coil size and hence reducing detection noise. Yet because coil sensitivity is proportional to the inverse of the radius of the enclosure, the detection SNR of this singular enclosure of both legs is much less than that of an enclosure of a single leg. However, imaging with smaller diameter coils placed separately around each leg suffers from SNR reduction due to inductive coupling between the coils.

The geometry of an anterior flexible array on both legs is described in U.S. Pat. No. 6,300,761, which reduces the distance between detection coil elements and anatomic parts by flexion onto each leg separately. Coil coupling between the right and left legs can be a serious issue. To alleviate this problem, decoupling circuits such as described in U.S. Pat. Nos. 5,489,847 and 5,708,361 can be used to enable proper coil function in this geometry of separate flexions onto both legs, and posterior surface of the lower extremity was not used for signal detection.

The geometry of an orthogonal separation between right and left is presented in U.S. Pat. Nos. 5,430,378 and 5,500,596 to minimize coupling interference between coil elements on the right and left legs. The orthogonality is maintained by orthogonality of coil planes, which prevents use of close distance between coil elements and anatomic parts.

The simple geometry of a pair of anterior-posterior plates is described in U.S. Pat. No. 6,323,648 and in Leiner et al, "Use of a three-station phased array coil to improve peripheral contrast-enhanced magnetic resonance angiography," J Magn Reson Imaging 2004; 20:417-425. This simple geometry is a straight-forward extension of the Roemer surface coil array design and has minimal optimization for improving SNR.

These surface coils all suffer from the problem of variable signal sensitivity which results in images where the artery may vary in signal intensity along its length even though there is no disease. This is a particularly difficult problem for post-processing the images to obtain maximum intensity projections or volume renderings which are generally very sensitive to image intensity variations. A superior coil from the signal homogeneity point of view is a volume coil or birdcage coil which tends to have favorable uniformity of signal intensity over the entire image. With two modes, quadrature detection is possible which reduces noise by the square root of two and thereby enhances SNR. However, these volume birdcage coils have several technical problems that limit their utility for peripheral MR angiography. Placing a separate birdcage coil around each leg causes a large loss in SNR from inductive coupling between the coils. On the other hand, a birdcage coil big enough to fit both legs tends to have poor SNR because of the large distance between tissue and coil for large sections of the coil. Another problem is that parallel imaging is not possible with birdcage coils. This results in either slower and lower resolution scans when using birdcage coils. These problems have been addressed by using conductive shielding in between the birdcage coils, but this solution reduces SNR, especially when the coils are close together such as the case for coils on right and left legs. Compared to surface coils, birdcage coils have lower SNR near the surface. However, this is not an issue for imaging arteries which tend to be deep to the skin surface.

Because of these challenges, there is a need for an improved peripheral vascular MR angiography coil which employs separate coils surrounding each leg to give high SNR, does not suffer signal loss from inductive coupling between the coils, provides a homogeneous signal or an inhomogenous signal with relatively greater sensitivity in the region of major arteries, and permits parallel imaging to reduce scan time and improve resolution.

SUMMARY

The present disclosure is directed to an MRI coil array that encloses each leg separately and circumferentially for minimal distance between detection coil elements and anatomic structures while decoupling the coils using shared reactive components for parallel elements, overlap and orthogonal element positioning.

In one aspect, a coil array includes a set of birdcage coils around each leg with at least two modes per birdcage coil. Each mode is perpendicular to at least one mode of the coil on the same leg and one mode on the contralateral leg coil to maximize decoupling of those modes. Modes which are parallel between right and left legs are decoupled by employing a shared reactive element such as a shared capacitor or shared inductor. Additional modes may allow for greater homogeneity of the birdcage coil signal sensitivity. The decoupling of the coils between the two legs allows for parallel imaging with simultaneous and independent imaging of each leg. This coil array is able to decouple elements sufficiently effectively that no conductive shielding is required to be placed in between coil elements, the lack of which contributes to high SNR.

In another aspect, a coil array includes multiple pairs of birdcage coils (or volume coils) optimized to fit around the thigh, calf and feet with a minimal distance separating the tissue from the coil elements. These pairs of birdcage coils can be decoupled through overlap. Typically overlap will be about 10% of the length of the each coil in the superior to inferior direction.

In another aspect, a coil array includes a birdcage-like geometry of surface coils positioned around the two legs in a FIG. 8 (or resembling an "infinity" symbol—∞—when positioned on a supine patient) configuration such that two medial elements are decoupled by orthogonal positioning and a pair of lateral elements is decoupled from the medial elements using overlap.

In yet another aspect, the decoupling of elements around the legs allows for parallel imaging which can permit shorter scan duration and/or higher scan resolution.

BRIEF DESCRIPTION OF THE DRAWINGS

FIGS. 10a-c illustrate measurements of impedance spectrum of the volume coils of FIG. 8. FIG. 10a depicts the impedance spectra of a single coil in isolation that is not coupled as evidenced by the single resonance peaks. FIG. 10b depicts the impedance spectra of two adjacent coils that are coupled as evidenced by the multiple resonant peaks. FIG. 10c depicts the impedance spectra of two adjacent coils that are decoupled by means of shared capacitors as evidenced by the single resonance peaks.

FIGS. 11a-11e illustrate individual coil element images obtained using: one volume coil of FIG. 8 in isolation with two phantoms present (FIG. 11a), two adjacent coupled volume coils of FIG. 8 (FIGS. 11b-c), and two adjacent decoupled volume coils of FIG. 8 (FIGS. 11d-e). FIG. 11f illustrates an image obtained using the body coil for RF excitation and reception, showing reduced sensitivity in the lateral portions of the phantoms.

DETAILED DESCRIPTION

1. Surface Coil Array for the Lower Extremities.

We outline here an approach to build a coil array for the lower extremity. The basic coil element is a rectangular coil bent onto a cylinder, so its size is characterized by its arc length and height. First, we determine the coil size optimal for a leg of given radius, which forms the building block for the peripheral coil array. Then we determine orthogonal or minimal-coupling configurations to assemble the coil elements for the entire lower extremity on an 8-RF-channel MR scanner.

First, we identify the optimal surface coil size for imaging the leg. The optimal size for a surface coil element is estimated by maximizing the SNR average while minimizing the SNR variation over a volume. The optimization is performed first numerically according to the principle of reciprocity (Wright S, Wald L, "Theory and application of array coils in MR spectroscopy," NMR Biomed. 1997; 10:394-410), $$SNR(r) \propto B^t(r) / [\int dV |A(r)|^2]^{1/2}. \quad [1]$$

Figure 1C:
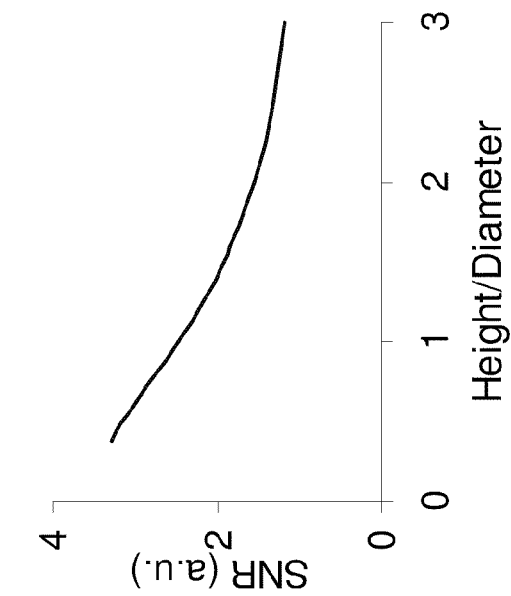
FIGS. 1b and 1c illustrate, respectively, that the SNR provided by the surface coil element in FIG. 1a within the cylinder volume is maximum at 180 degree arc length and decreases with the height/diameter ratio.
Figure 1B:
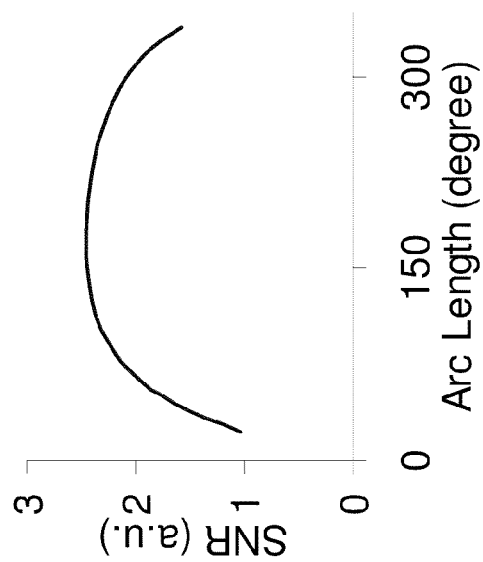
Figure 1A:
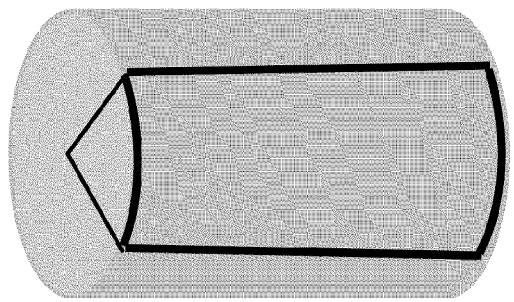
FIG. 1a is a schematic representation of a surface coil element on a leg modeled as a cylinder.

Here $B^t$ and $A$ are the transverse component and the vector potential of the magnetic field produced by a unit current in the coil (the volume integral is over the whole leg). Calculation in the case of uniform cylinder (FIGS. 1a-c) indicates that the optimal arch length is 180° and the desired height-to-diameter ratio is as small as possible. (The average sensitivity ($<B^t>$) is approximately invariant with height/diameter ratio, but more noise for taller coils results in SNR decreases with height, FIG. 1c).

Second, we identify an array configuration to minimize coil coupling between two legs. A challenge to build a coil array for the lower extremity is to reduce coil coupling between the two legs. In addition to the standard method (overlapping adjacent coils and use of low input impedance preamplifiers for each coil), we seek two ways to minimize the inter-leg coupling: the x-configuration (medial coil array) based on orthogonal coil intersection (FIG. 2a), and the ( )-configuration configuration (lateral coil array) by maximizing the separation between the left and right legs (FIG. 2b). Both can be combined to form the ∞-configuration (FIG. 2c), in which coil element 1 is decoupled with elements 2&3 through partial overlapping and minimally-coupled with element 4, element 2 is decoupled with elements 1&4 and almost decoupled with element 3, etc. A shared capacitor or inductor can be used to eliminate residual coupling among coil elements. For the coil design, we perform numerical SNR calculation for these configurations. Coil interactions are characterized by the mutual impedance between two coils such as coil a and coil b:

$$Z_{ab} = \sigma \omega^2 \int dV A_a(r) \cdot A_b(r) + i\omega \int_a dl I_a(r) \cdot A_b(r) = R_{ab} + iX_{ab}, \quad [2]$$

here the volume integral is over the sample and the line integral is over coil a, $A_a$ is the vector potential due to unit current $I_a$ in coil a, etc. Signal from individual coil $S_a(r)$ are combined in an optimal way accounting for both magnitude and phase effects, $$S(r) = \Sigma_{ab} S_a(r) R^{-1}_{ab} B^t_b{}^*(r), \quad SNR = (\Sigma_{ab} B_a R^{-1}_{ab} B^t_b{}^*)^{1/2}. \quad [3]$$

Eq. 3 can be used to simulate coil design for maximizing SNR improvement.

Figure 2A:
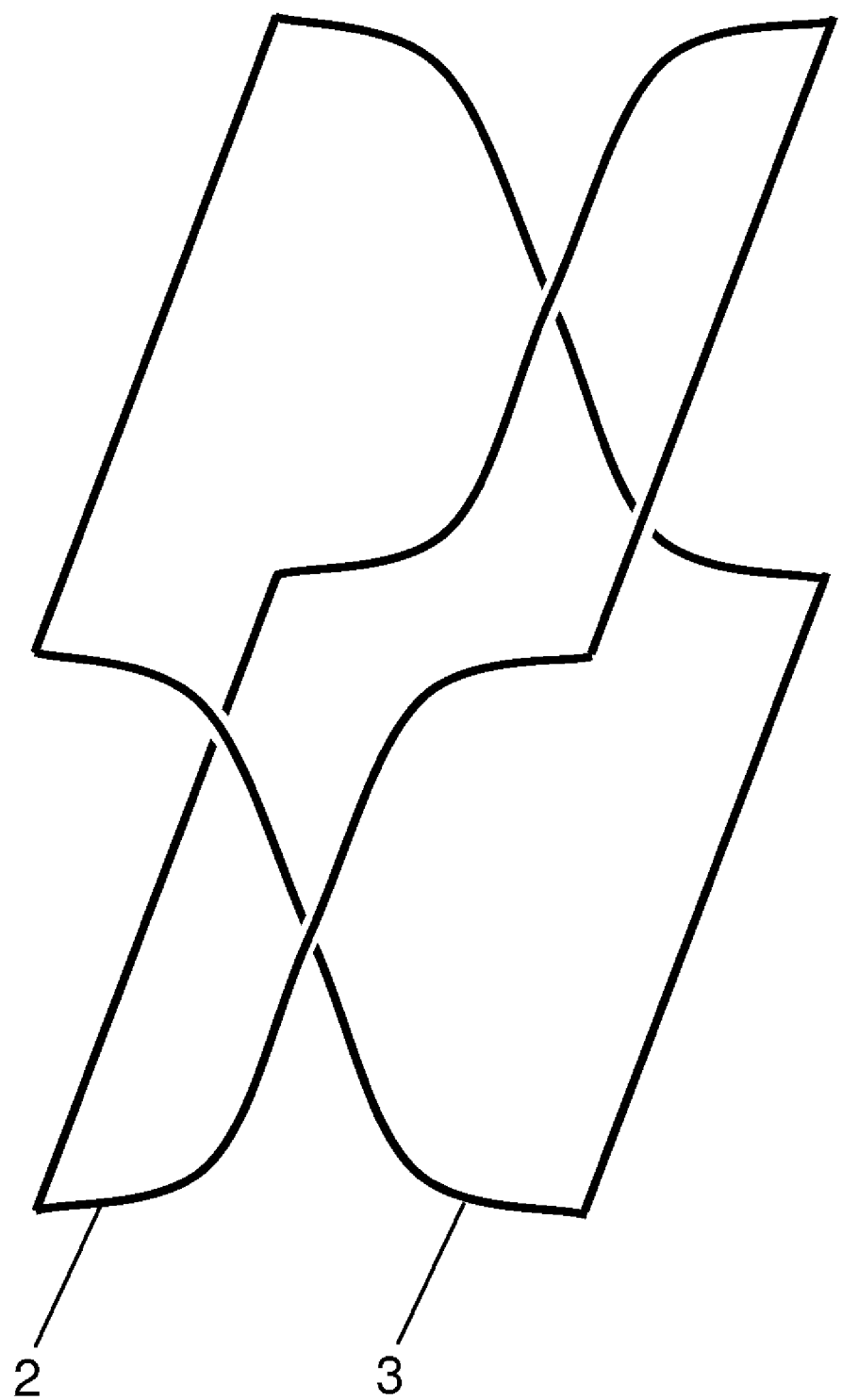
FIGS. 2a-2c are, collectively, a schematic representation of the phased-array lower extremity coil, referred to as the infinity (∞) array, which includes medial orthogonal elements, referred to as the x elements, and lateral elements referred to as the c elements.
Figure 2B:
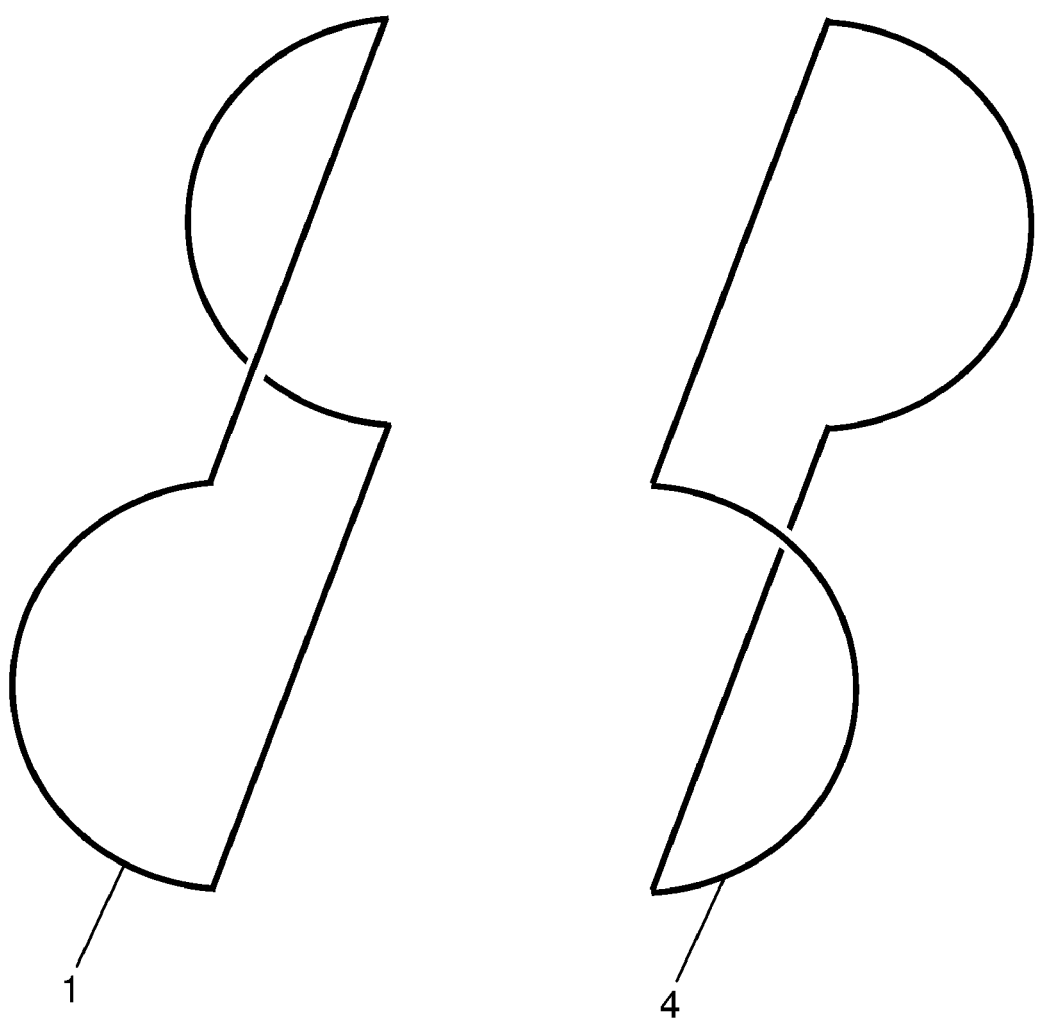
Figure 2C:
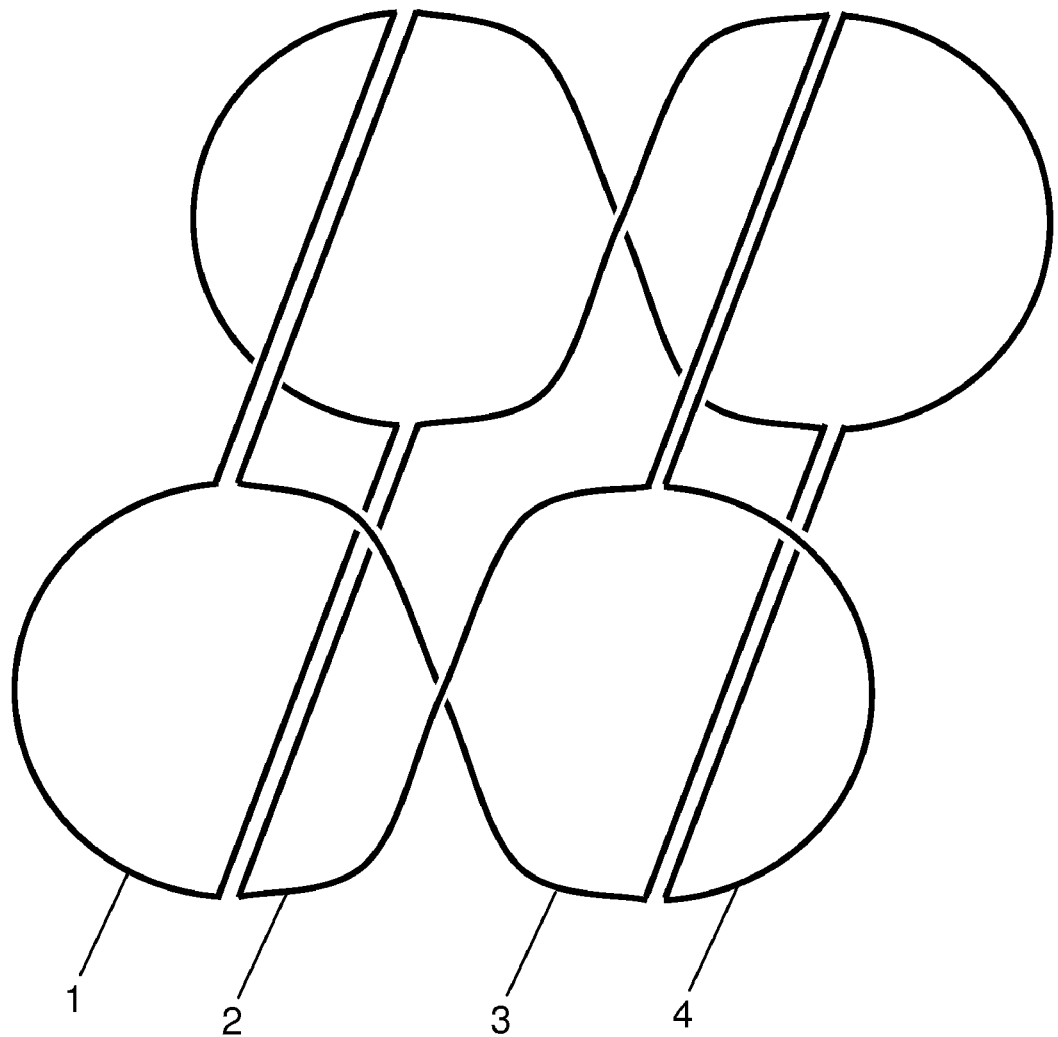

The x- and ( )-array in FIGS. 2a-b each provides an SNR=1.43×$SNR_{PV}$ (SNR of the current Peripheral Vascular coil), and the sum of them is the ∞-array in FIG. 2c, which provides an SNR ~1.43*√2~2×$SNR_{PV}$. With coil height/diameter reduced by half, SNR of the ∞-coil array developed here is 2.8×$SNR_{PV}$ (more than 100% increase). Note that the ∞-array has an inhomogeneous sensitivity over imaging FOV. Its hot spots are located above and below the native arteries in a leg, to the advantage of peripheral MRA. Although usually uniform sensitivity is preferred for MRA, if there is inhomogeneous sensitivity then having the greatest sensitivity over the region of vessels (especially major arteries) is preferred. This represents an advantage over existing surface coil designs where the greatest sensitivity is at the skin surface.

Figures 3A, 3B, 3C, 3D:
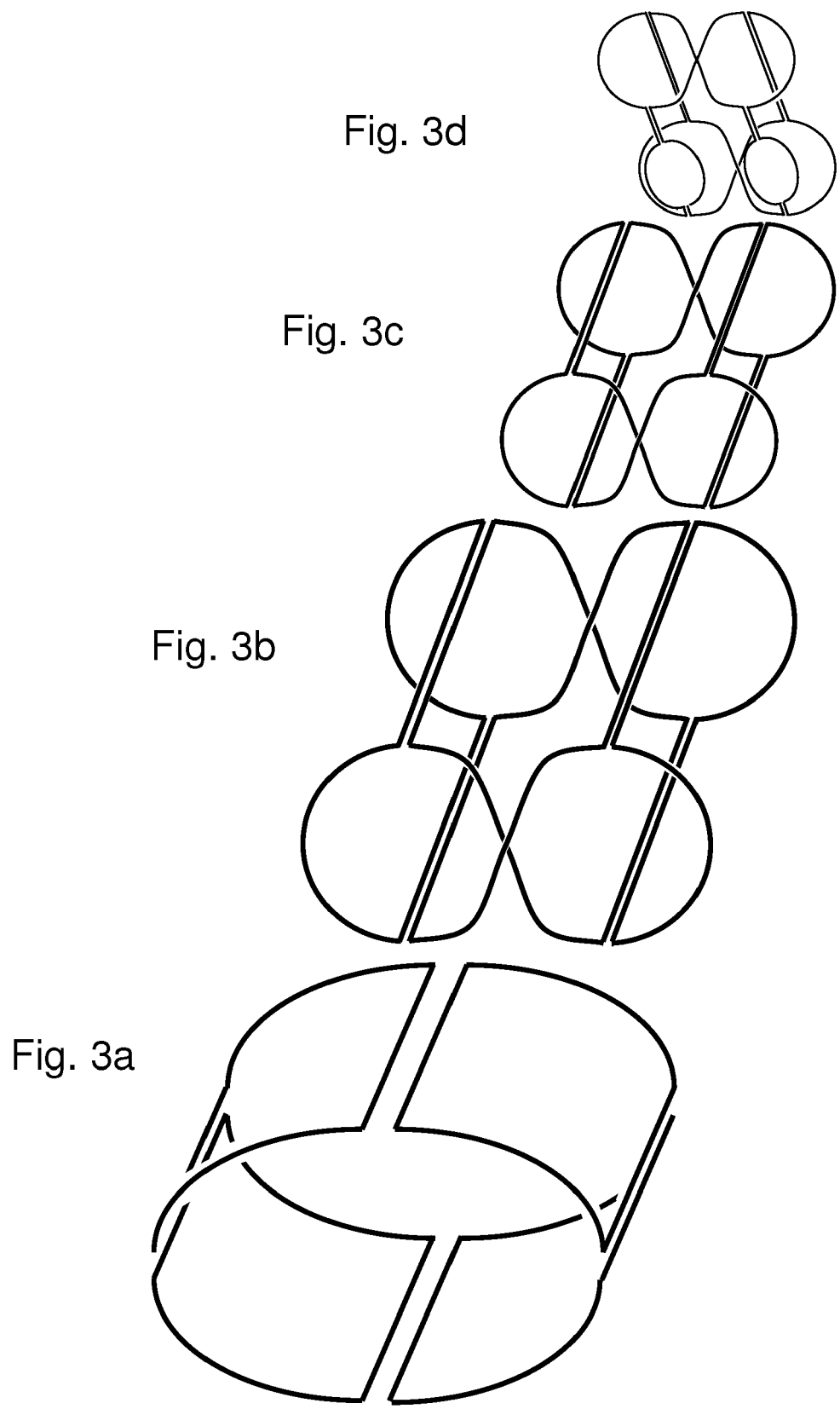
FIGS. 3a-3d are schematic representations of 4-channel arrays for the abdomen using flexed anterior-posterior array plates (FIG. 3a), thigh and calf using horizontal ∞-coil arrays (FIGS. 3b and 3c respectively) and feet using a vertical ∞-coil array (FIG. 3d).
Figure 3E:
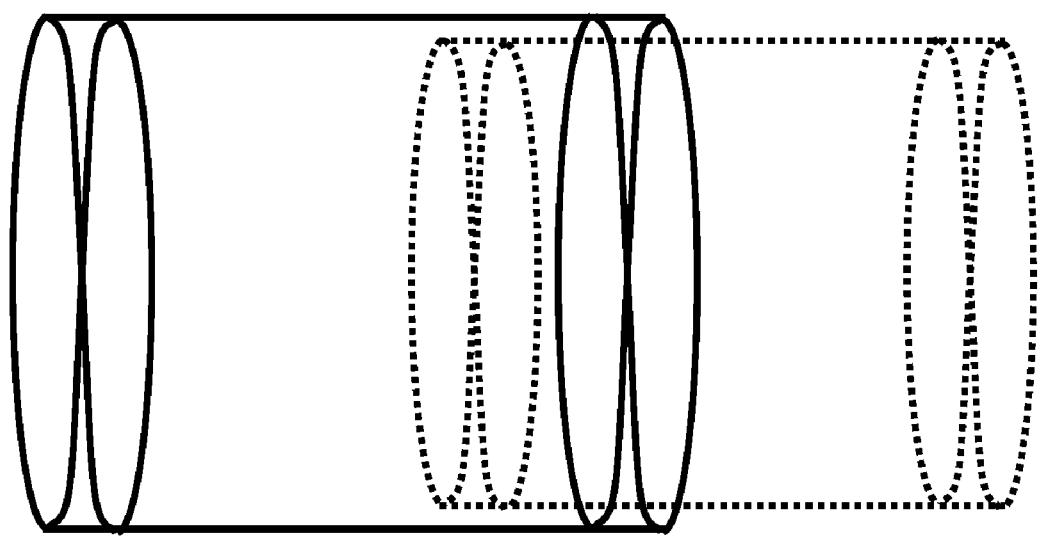
FIG. 3e is a schematic representation of a pair of ∞-coil arrays, with a superior-inferior overlap.

Finally we construct coil array "pants" for the whole extremity. The same optimization procedure defined by the above Eqs. 2&3 are used to optimize coil arrays for the feet and abdomen. The standard torso coil is likely very close to the optimal for the abdomen. The feet can be fitted with a vertical ∞-configuration (FIG. 3d). The contour of the coil array must be deformed to fit the ankle tightly.

After optimizing the coil array for the 4 parts of the lower extremity (abdomen, thigh, calf and feet), we assemble them as a pair of coil pants. A configuration for the coil pants is shown in FIGS. 3a-d for the case of 4 RF reception channels. The whole of the lower extremities (a 90-120 cm cranial-caudal extent) is imaged with 4 stations of varying and overlapping FOV. Accordingly, the coil pants are segmented into 4 parts: abdomen, thigh, calf, feet. Each segment can be covered by a single 4-channel array as shown, or each segment can include two overlapping coil arrays for a total of 8 channels. The 4-channel arrangement is shown for simplicity. Two different sizes of coil arrays are used to cover the upper and lower legs. The coil pant is adjusted to fit patients of various heights. An electric switch is employed to selectively activate the desired part of the coil pants. The other parts in the coil pants are isolated with a dc bias to prevent any interference to the activated part.

Figure 2D:
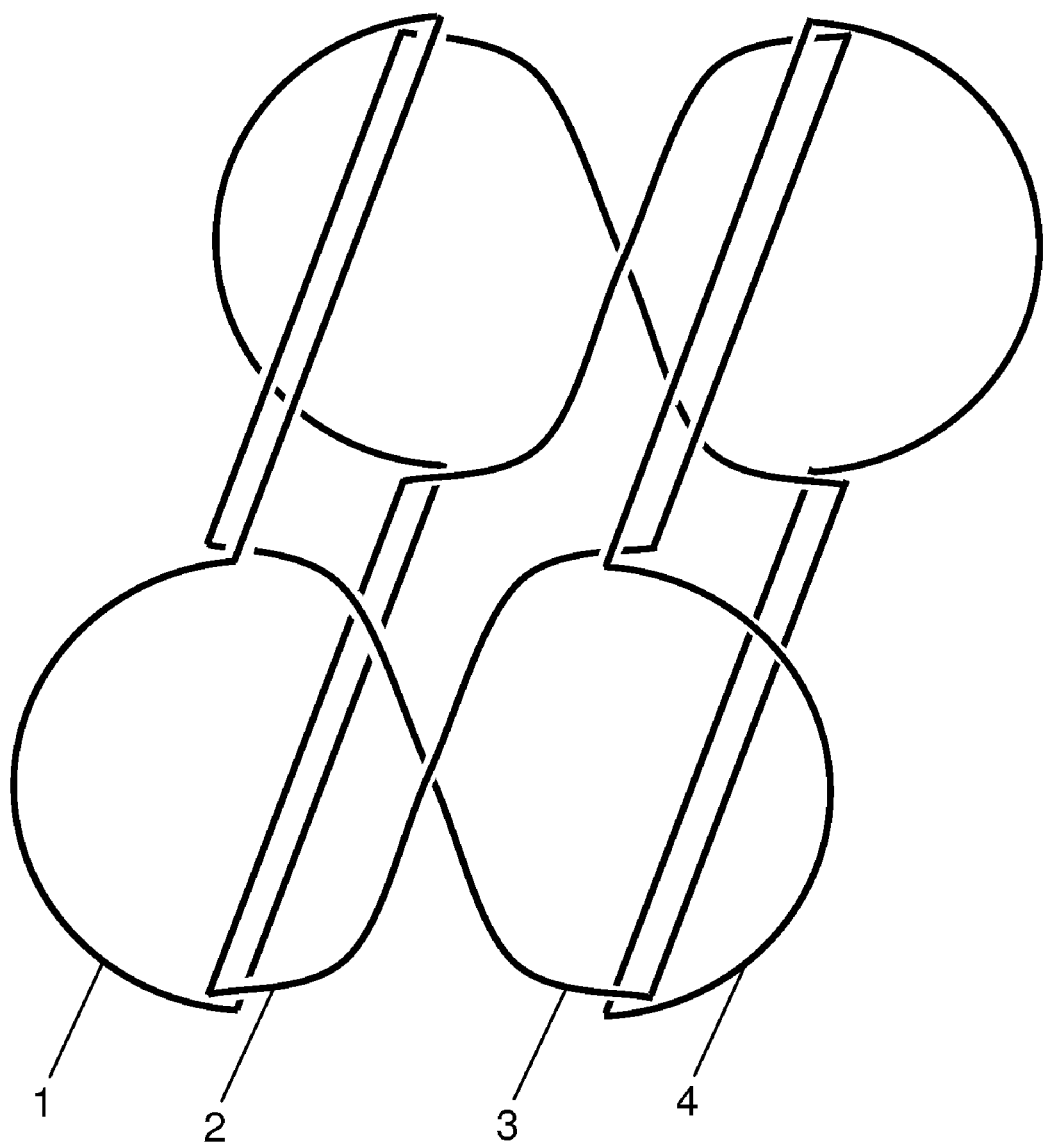
FIG. 2d is a schematic representation of an ∞-array arranged so that each lateral element overlaps with the medial elements.

The ∞-coil (FIG. 2c) is constructed by combining the x-coil with the ( )-coil. All 4 coil elements are build on two acrylic cylinders (one for each leg). Each element has the following approximate dimensions: radius/height/overlap≈10/20/2 cm for the thigh elements, 6.5/20/2 cm for the calf elements, 5.5/16/2 cm for the feet elements. These radius/height dimensions are selected to accommodate 99% of the population (Tiller AR, "The measure of man and woman," New York: The Whitney Library of Design, 1993). Appropriate partial overlap between the x- and ( ) components in the ∞ coil, as shown in FIG. 2d, is used to minimize their mutual inductance.

For the ∞-coil array pants (FIGS. 3b-d), more than one coil can be used for each segment, so that the abdomen could be covered by two coaxial, overlapping torso coil arrays, the thigh could be covered by two overlapping horizontal thigh ∞-coil arrays, the calf could be covered by two overlapping horizontal calf ∞-coil arrays, and the feet could be covered by two overlapping vertical foot ∞-coil arrays. Appropriate partial overlapping between adjacent ∞-coil sets is used to minimize the mutual inductance between them.

Figure 4:
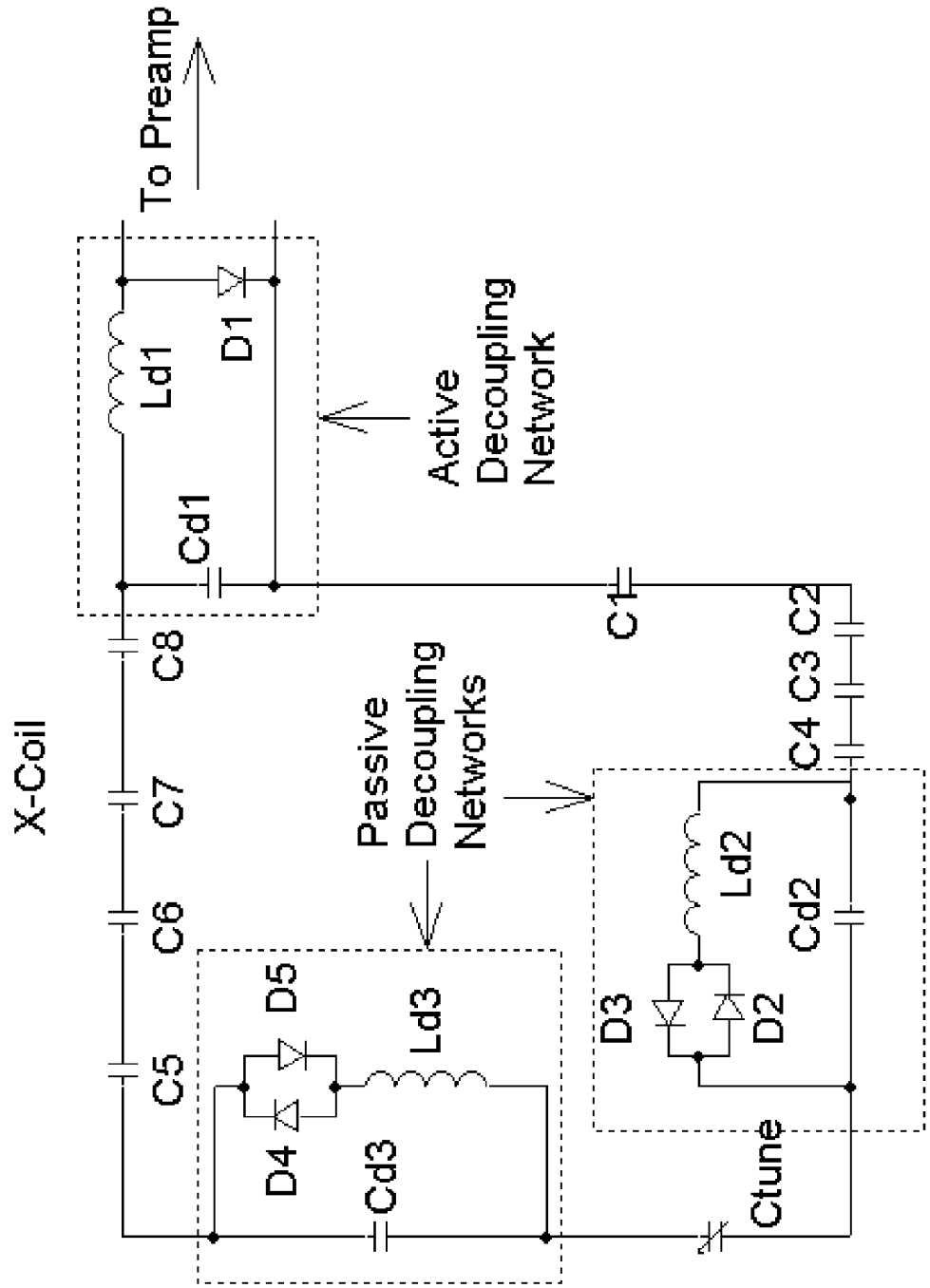
FIG. 4 is a schematic diagram of the electrical components within a single coil element of FIGS. 2a-c.

Coil elements are constructed with distributed capacitors to minimize electric fields, thus reducing the effect of patient load on the resonance frequency. The ( )-coil is constructed according to standard receiver surface coil electronics. A schematic of one x-coil element is shown in FIG. 4. A variable capacitor ($C_{tune}$) is placed in series with the chip capacitors to allow tuning of the coil. The matching capacitor ($C_{dl}$) transforms the real impedance of the coil to 50Ω.

Each coil set is tuned to 63.87 MHz (for imaging at 1.5 T) and matched to approximately 50Ω with two long cylindrical leg phantoms placed within the coil. Leg phantom: 10 cm radius, 90 cm length, copper sulfate doped water, T1~70 ms, approximating leg loading.

The body coil is used for RF transmission to provide homogeneous excitation field over the FOV. The receive-only coils are decoupled from the transmit coil during excitation using both active and passive decoupling networks. The active decoupling network uses a forward biased pin diode $D_1$ to create a tank circuit. During RF transmission, the MRI system applies forward bias to $D_1$ in FIG. 4, effectively making the diode a short circuit. To supplement the active decoupling network, two passive decoupling networks were included to provide added safety in the event of an active decoupling network failure. Each passive network uses a crossed diode pair ($D_2$ & $D_3$, $D_4$ & $D_5$ in FIG. 4) to create a tank circuit. During RF transmission, sufficient RF voltage is presented (greater than 0.7V) to turn on the crossed diodes. Thus, the tank circuit is inserted in series with the coil, making the coil inactive. During RF reception, the RF voltage is too small to turn the diodes on. Thus, each diode in the crossed pair is effectively an open circuit and the coil is active.

In order to facilitate positioning patient legs into the coil pants, both the ∞- and birdcage coils are constructed with a split connection such that the coils are separated at their meridian into an anterior and posterior part (thigh and calf) or left and right part (feet). The coil split introduces negligible disturbance to current path and coil performance.

2. Birdcage Coil Array for the Lower Extremity.

The birdcage coil can provide high & uniform sensitivity which is favorable for MR Angiography. Its cylindrical shape provides a good fit for an individual leg. Two birdcage coils (one for each leg) are used to image both legs simultaneously. To cover the entire lower extremity & to further improve SNR, we construct birdcage arrays and then birdcage pants.

The sensitivity of the birdcage coil is $$B^t = 2a^{-1}h(2+h^2)(1+h^2)^{-3/2}N \sin \pi/N, \qquad [4]$$

where a is the coil radius, h is the height/diameter, N is the number of straight legs (normally=16). $B^t \sim 2\pi a^{-1}$, i.e., approximately independent of N and h (height). Our prototype calf birdcage coil provided a SNR improvement over the head coil close to the prediction by Eq. 4: $a_{head}/a_{calf} = 11.125/6 = 1.85$, $SNR_{calf}/SNR_{head} = 1.77$.

Figure 5B:
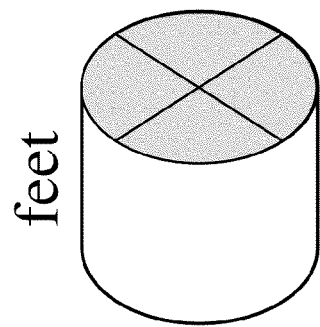
FIG. 5b illustrates a single coil with end cap for feet imaging.
Figure 5A:
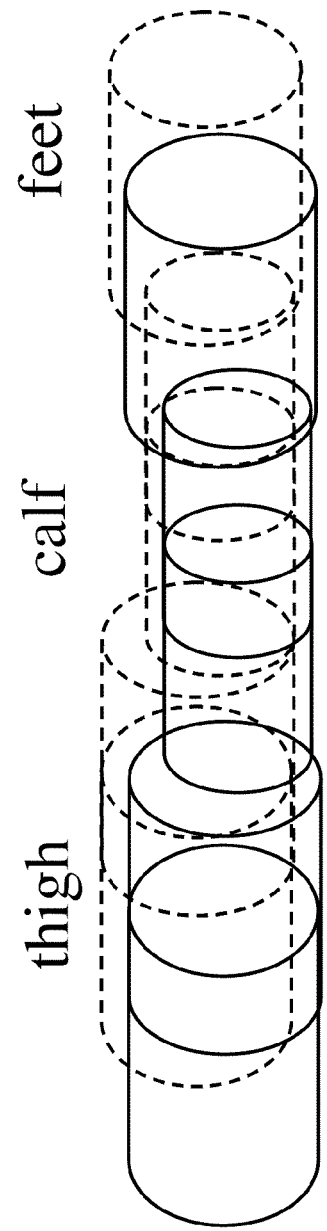
FIG. 5a is a schematic representation of a pair of birdcage-array "pants" from the thigh to the feet.

Similar to the surface coil, noise in a birdcage coil increases with its height, and consequently SNR decreases with height. For optimal SNR, an array of two short birdcages is used to cover one thigh or calf, and two such arrays are connected into an 8-channel RF system for simultaneous imaging of two thighs or two calves (FIG. 5a).

Figure 8B:
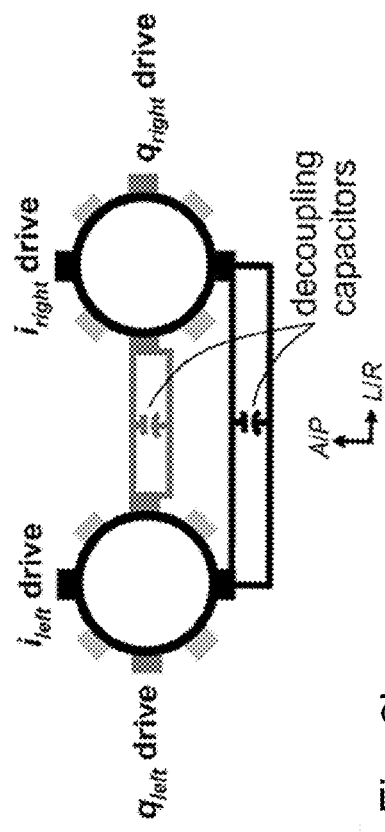
FIG. 8b depicts the volume coil orientation such that the i and q channels are orthogonal. i channels rods are in black, q in dark gray, and balancing rods in light gray. Decoupling capacitors are also shown for reference.
Figure 9A:
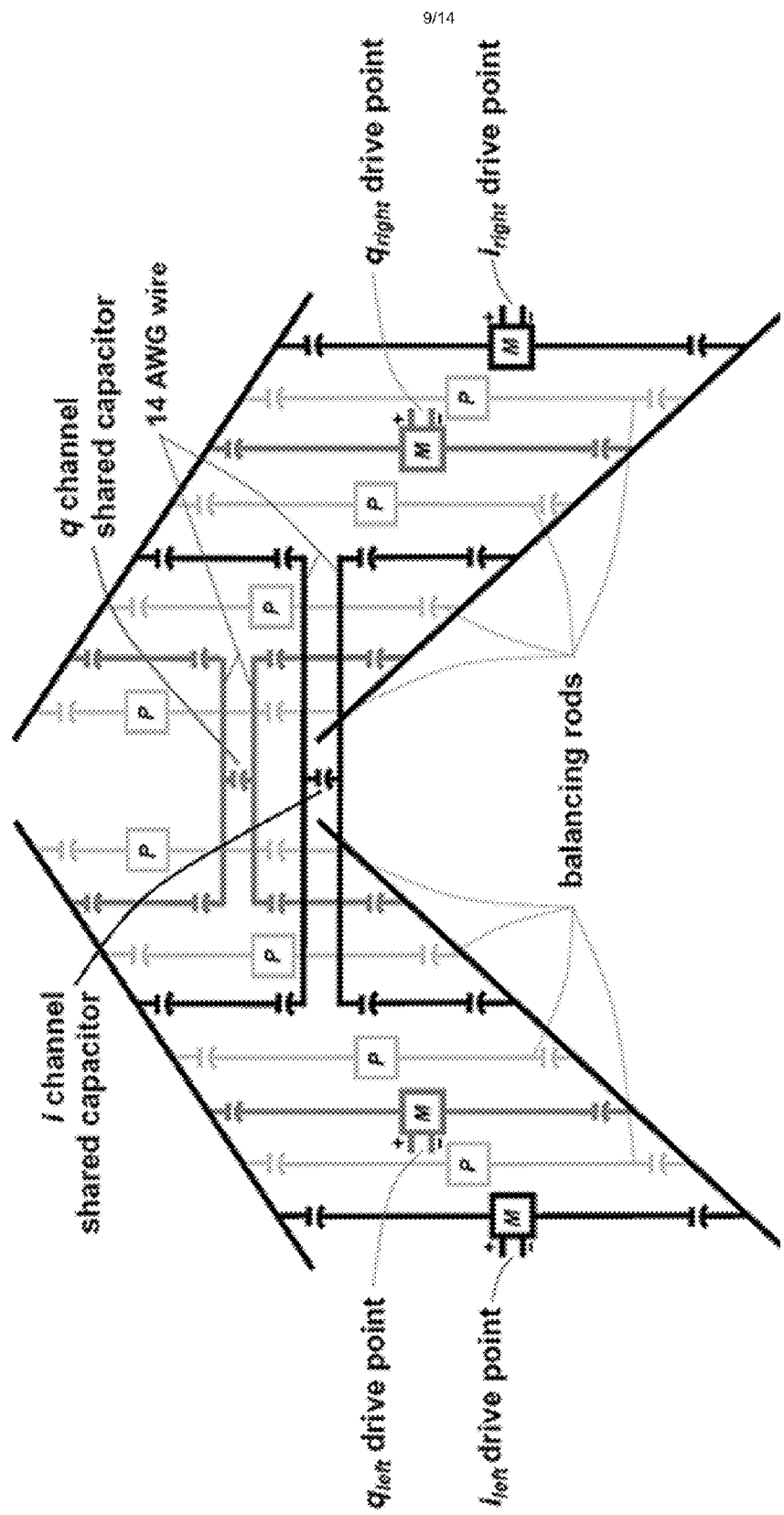
FIG. 9a is a schematic diagram of the electrical components of two adjacent volume coils of FIGS. 8a-b in accordance with an exemplary embodiment of the invention. Decoupling capacitors are used to eliminate mutual inductance between adjacent coils.

As in surface coil array, a major challenge in constructing birdcage arrays is to minimize coupling between birdcages, which may be achieved through coil overlapping and relative rod positioning. The birdcage array for the right leg is decoupled from the birdcage array for the left leg using a capacitor, or inductor, or a combination of them to minimize right left coupling as illustrated in FIG. 8b and FIG. 9a. The vertical and horizontal modes in a birdcage on the right leg only couples to correspondingly vertical and horizontal modes in a birdcage on the left leg respectively. Accordingly decoupling only needs to be implemented on these two parallel modes. The shielding method that also allows decoupling of the right and left birdcages has the disadvantage of reduced SNR because the coil induces an opposing current in the shield. An RF transmission splitter can be used to drive the two birdcages simultaneously, or the body coil can be used for RF transmission and the birdcage array can be used for RF reception only.

Two or more birdcage arrays may be positioned to cover the whole thigh and calf. The superior and inferior birdcages on the same leg are best decoupled by overlapping, because overlapping allows uniform SNR detection at overlapping area. A birdcage array with orifice opening for toes or a single birdcage may be used to image the foot. An end cap is attached to the foot birdcage to double its electronic length and increase its sensitivity. A pair of coil pants made of birdcage is shown in FIG. 5a. The feet can be covered with two birdcages (FIG. 5a) or a single birdcage (FIG. 5b), and end caption can be used to increase SNR at the feet.

Figure 6:
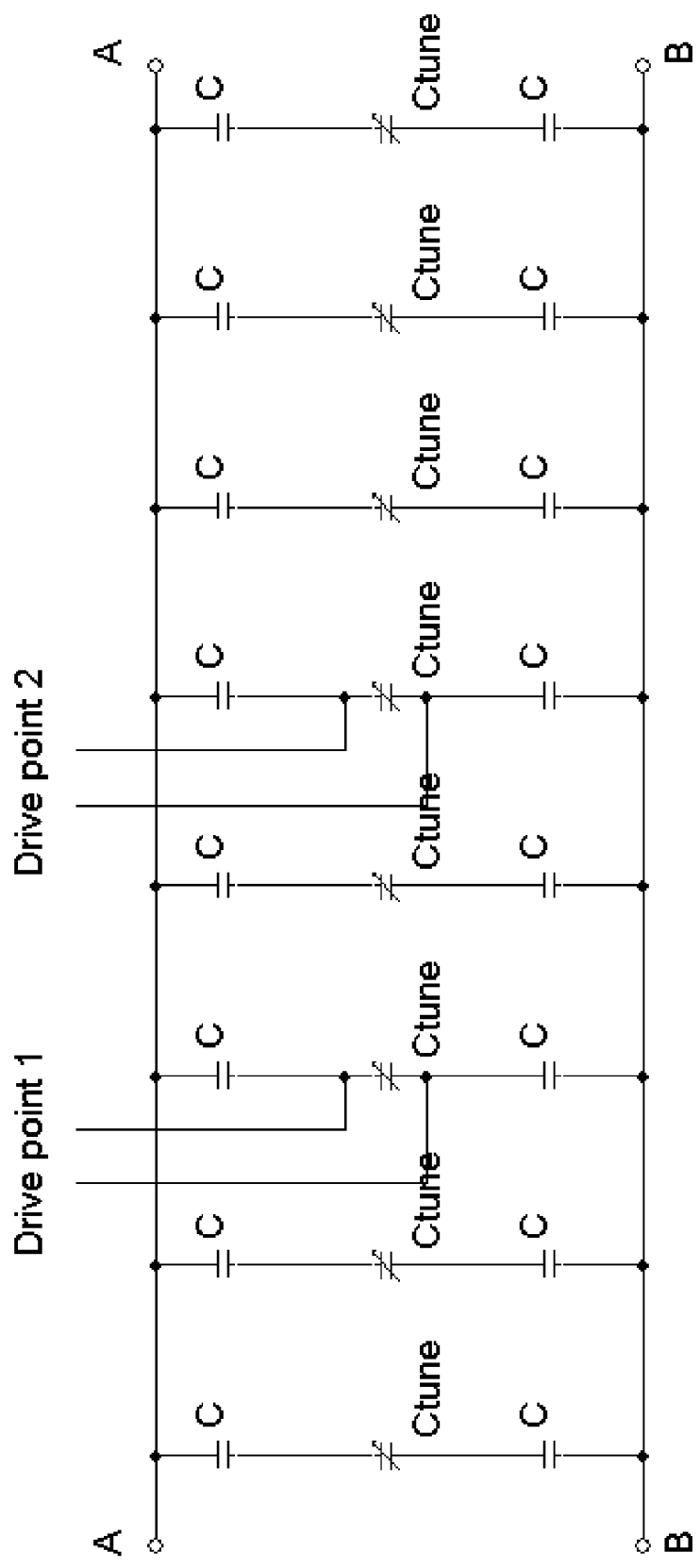
FIG. 6 illustrates electronic schematics for a birdcage coil.

The birdcage array is built on acrylic cylinders. Each element is a low-pass birdcage with 8 rods. Two birdcages are used to cover each of the thighs and calves, while one birdcage is used to cover the feet. The birdcages have the following approximate dimensions: radius/height/overlap≈10/20/2 cm for thigh elements, 6.5/20/2 cm for calf elements; for feet element: radius≈15 cm, height≈10 cm. These radius/height dimensions are selected to accommodate 99% population. Quadrature operation is achieved by placing two drive points 90° apart (FIG. 6). Superior birdcages are partially overlapped with their inferior neighbor to minimize the mutual inductance between them. In order to minimize mutual inductance between adjacent birdcages a RF shield or a capacitor or an inductor is placed between them.

The capacitance per birdcage is calculated using the following formula (Leifer MC, "Resonant modes of the birdcage", J Magn Reson Imaging 1996; 124:51): $C = 2(1-\cos 2\pi/n)/m\omega^2$, n=number of rods, m=mutual inductance between rods, ω=resonance frequency. The capacitor in each rod is distributed to minimize patient loading effects. A variable capacitor ($C_{tune}$) is placed in series with the chip capacitors (C) to allow tuning of the coil (FIG. 6). Each coil is tuned to 63.87 MHz (1.5 T) and matched to 50Ω with the cylindrical phantom (described above) placed within the birdcage.

In order to facilitate positioning patient legs into the coil pants, the birdcage coils are constructed with a split connection such that the coils are separated at their meridian into an anterior and a posterior part (thigh and calf) with negligible disturbance to current path and coil performance.

3. Hybrid Coil Pants made of Surface Arrays and Birdcages.

Figure 7:
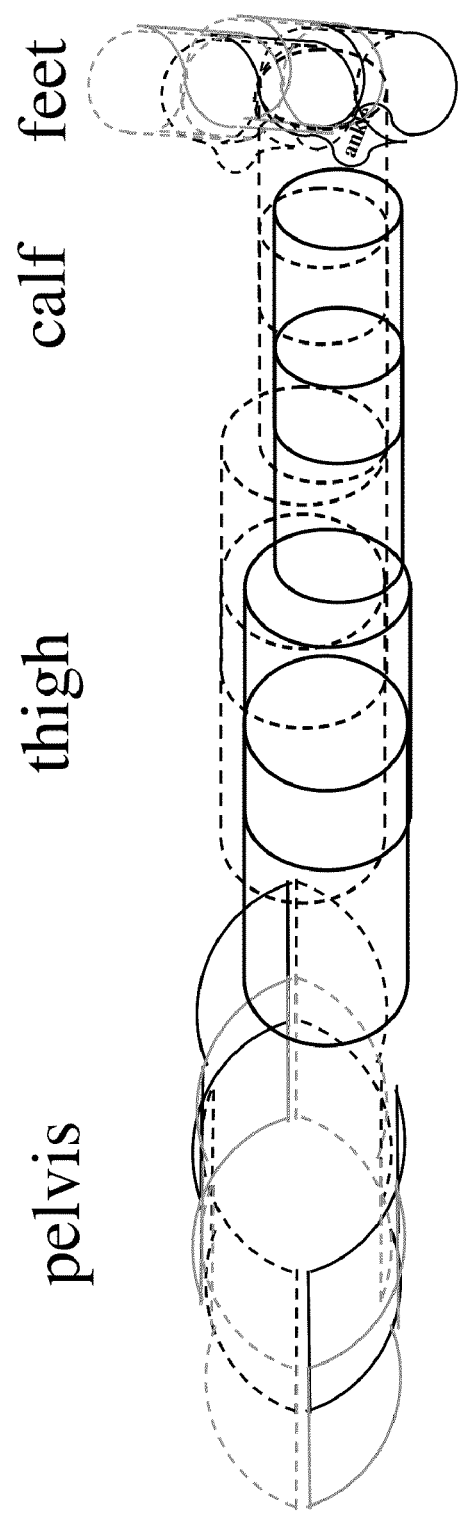
FIG. 7 is a schematic representation of hybrid coil pants using the surface array for the pelvis of FIG. 3a, birdcage arrays for the thighs and calves of FIG. 7a, and vertical ∞-array for the feet of FIG. 3d.

The birdcage array offers the benefit of high and uniform sensitivity for the thigh and calf, and the surface array offers the benefit of high SNR for the abdomen and feet. For optimal SNR in all stations of the lower extremity, the corresponding parts in FIGS. 3a-b and 5a can be assembled together to form a pair of hybrid coil pants as illustrated in FIG. 7.

4. A Peripheral MRA Experimental Study with Birdcage Arrays for Imaging the Lower Extremities.

We introduced an array having multiple birdcage coils and compared this design to commercially available coils. The constructed birdcage array was utilized for peripheral magnetic resonance angiography (MRA). MRA has been revolutionized by the bolus chase technique in which a single bolus injection is imaged multiple times as it travels down the peripheral arteries. This technique overcomes the normal FOV limitations of MR scanning but presents significant design challenges for receiver coils. Historically, bolus chase experiments employed the large body coil or torso coil for signal reception (Ho KY et al., "Peripheral vascular tree stenoses: evaluation with moving-bed infusion-tracking MR angiography," Radiology 1998; 206(3):683-692. Wang Y, et al., "Bolus-chase MR digital subtraction angiography in the lower extremity," Radiology 1998; 207(1):263-269). While this approach simplified image data acquisition, image quality was limited by poor SNR associated with the large body coil. Nonetheless, the body coil proved acceptable for imaging large arteries in the abdomen/pelvis and thighs. However, higher SNR was required to resolve smaller arteries in the calves and feet. To remedy this problem, several groups have introduced dedicated phased array surface coils specifically designed for lower extremity imaging (U.S. Pat. Nos. 5,548,218, 6,137,291, 6,438,402, 6,300,761, 5,430,378, 5,500,596, and 6,323,648. Leiner et al., "Use of a three-station phased array coil to improve peripheral contrast-enhanced magnetic resonance angiography," J Magn Reson Imaging 2004; 20:417-425). The work presented here utilizes birdcages for signal reception, which can provide advantages over surface coils. Specifically, quadrature detection, which improves sensitivity by √2 over linear coils, is obtained throughout the birdcage volume compared to surface arrays, in which quadrature is achieved only in localized regions. On the other hand, surface coils can provide high sensitivity at small imaging depths. However, this is of lesser importance for lower extremity MRA, as the arteries typically lie toward the center of the legs.

A major challenge in the birdcage array design is resonant frequency splitting caused by coupling. Several decoupling methods for surface coil arrays have been established (U.S. Pat. Nos. 4,825,162, 5,489,847 and 5,708,361), but there has been little investigation on the isolation of volume coils in human imaging. The array described here utilizes shared capacitors between adjacent birdcages to reduce magnetic coupling. Descriptions and results of the decoupling method including bench measurements and MR images are given here.

Figure 8A:
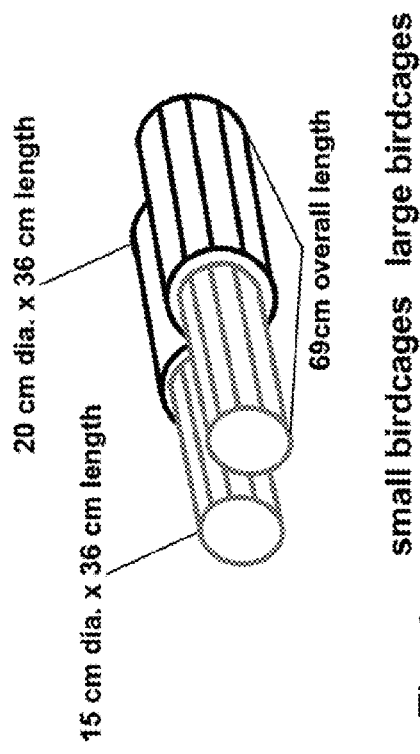
FIG. 8a is a schematic representation of a volume coil array that includes two sets of adjacent quadrature volume coils.
Figure 8C:
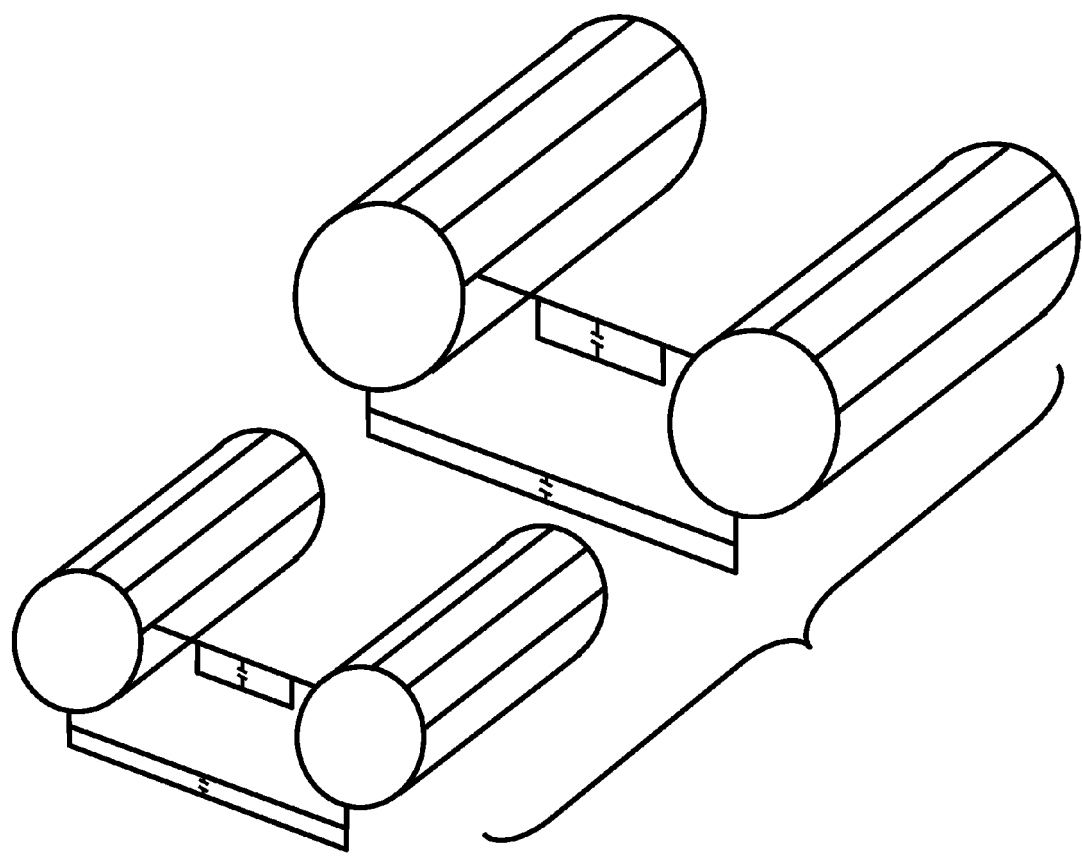
FIG. 8c is a schematic exploded representation of a volume coil array that includes two sets of adjacent quadrature volume coils interconnected by decoupling capacitors.

The central objective of this study was to magnetically decouple adjacent birdcage coils in order to utilize the array for lower extremity angiography. The prototype array included four birdcages (see FIG. 8a): two 20 cm diameter, 36 cm long birdcages suitable for imaging the thighs or feet (referred to as the large birdcage set) and two 15 cm diameter, 36 cm long birdcages to cover the calves (referred to as the small birdcage set). The coils were large enough in diameter to accommodate a large percentage of the population while keeping in mind that smaller coils achieve higher sensitivity. Standard charts of the human anatomy were used for guidance, which reported a thigh diameter of 20 cm or less and calf diameter of 11 cm or less for 99% of the population. To make patient entry more convenient, the coils were split along their median to allow the top hemisphere to swing open during patient positioning. This split required a partition in each end ring which was joined using an SMA connector (Amphenol RF, Danbury, Conn.).

The coils were laid out using 2.54 cm wide copper tape on acrylic formers. An eight rod low pass design was used (see FIGS. 8a-b & 9a). Fixed value (100B series, American Technical Ceramics, Huntington Station, N.Y.) and variable capacitors (NMA series, Voltronics Corp., Denville, N.J.) were distributed along each rod to tune each coil to 63.87 MHz and to reduce electric field losses. The coils were capacitively matched to 50Ω while loaded with a 3.2 L cylindrical phantom (12.7 cm diameter) filled with distilled water and doped with 10 mMol $CuSO_4$ and 60 mMol NaCl to approximate leg loading. The small and large birdcages were found to have quality factors (Q) of, respectively: 320, 335 (unloaded); 25, 35 (phantom load); and approximately 40, 25 (human leg load). The high $Q_{unloaded}$ to $Q_{loaded}$ ratio indicates good performance and sample noise dominance.

Figure 9B:
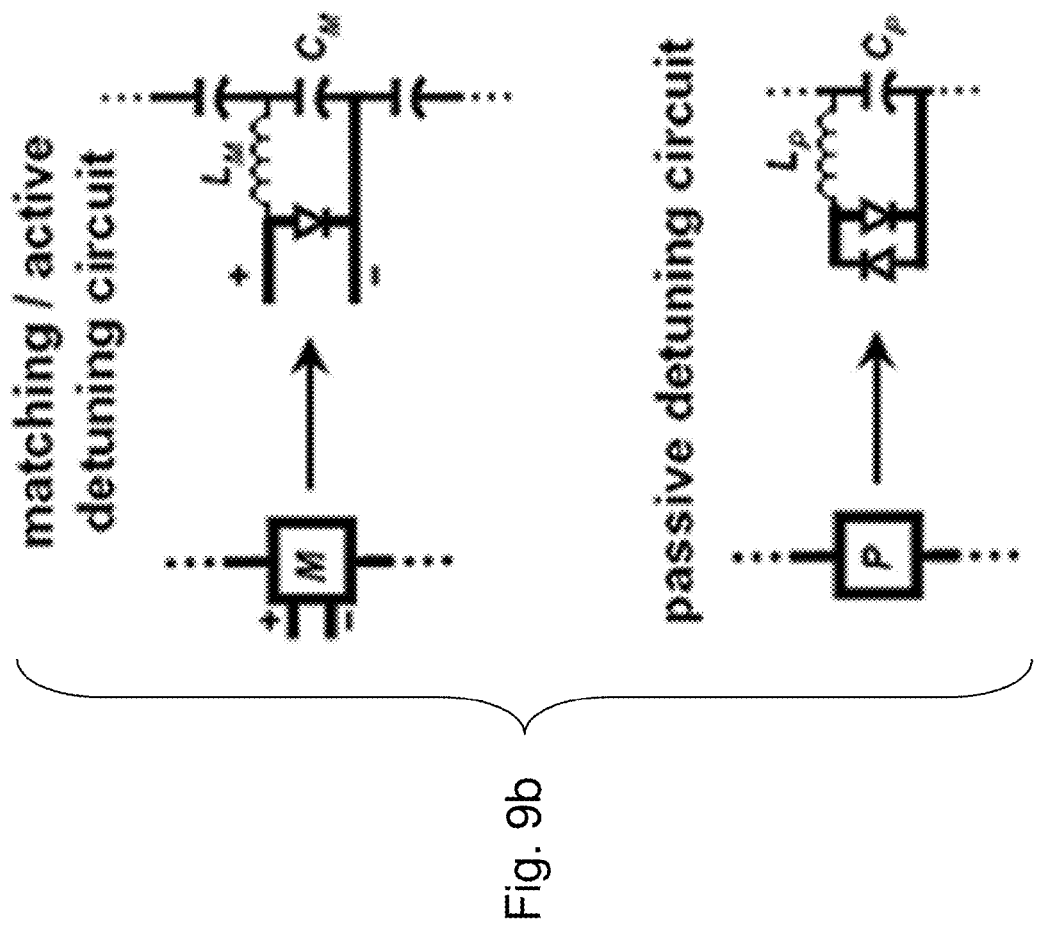
FIG. 9b details the capacitive matching and detuning circuitry. Capacitor/inductor pairs $C_M/L_M$ and $C_P/L_P$ have equal but opposite reactance ($j\omega L = -j/\omega C$) such that a high impedance blocking circuit is formed when the corresponding diode is on to deactivate the coil during RF transmission.

After the individual birdcages were tuned, they were positioned side-by-side and affixed to a common former with a center-to-center spacing of 22.5 cm. As expected, magnetic coupling caused resonant frequency splitting. To simplify the decoupling task, the array was orientated such that heavy coupling was constrained to two parallel channel combinations ($i_{left}$-$i_{right}$ & $q_{left}$-$q_{right}$) while the orthogonal channel combinations ($i_{left}$-$q_{left}$, $i_{left}$-$q_{right}$, $i_{right}$-$q_{right}$, $i_{right}$-$q_{left}$) were naturally well-isolated (FIG. 8b). Furthermore, given the sinusoidal current distribution inherent to the birdcage, this orientation allowed the i and q channels to be independently decoupled. Coupling between i (q) channels was removed by introducing a shared capacitor between rods 180° from the i (q) drive rods (FIGS. 9a-b). Relatively large 0.17 cm diameter wire (14 AWG) was used to connect the shared capacitors, as the path between channels was quite long: 22.5 cm between q channels and 4 cm (7.5 cm) between i channels of the large (small) birdcages. An extra distributed capacitor was added to the decoupling rods to reduce current asymmetry resulting from this decoupling circuitry, although the circuitry still caused the resonant frequency of each channel to shift slightly. This was restored to 63.87 MHz by iteratively adjusting both the capacitors on those rods to which the shared capacitors were added as well as the shared capacitors themselves. Finally, minor adjustments were made to the balancing capacitors (which can compensate for an imperfect sinusoidal current distribution around the birdcage) to restore the orthogonality of each birdcage ($i_{left}$-$q_{left}$ & $i_{right}$-$q_{right}$). No specific action was taken to isolate channel pairs $i_{left}$-$q_{right}$ or $i_{right}$-$q_{left}$, as only moderate coupling was present.

A network analyzer (model 5070B, Agilent Technologies, Palo Alto, Calif.) was used to characterize coupling by measuring the transmission coefficient $$S_{21} = \frac{V_2^-}{V_1^+},$$

where $V_1^+$ indicates the amplitude of the incident wave driven into port 1 and $V_2^-$ the amplitude of the measured wave coming out of port 2. Impedance (Z=V/I) spectra were also recorded to demonstrate coil resonance. MR images were obtained from individual birdcage elements to further evaluate coil coupling.

The primary application for the birdcage array was bolus chase angiography of the lower extremities which required a long superior/inferior (S/I) FOV. This was accomplished by joining the two birdcage sets as in FIG. 8a. Coupling between S/I neighbors was reduced to less than −20 dB by partially overlapping the coil sets by about 3 cm. Bolus chase experiments also required switching between the large and small birdcage sets according to the active imaging station. It proved convenient to adapt the coils to operate in receive-only mode as this configuration enabled the use of standard scanner software to manipulate coil activity. This was carried out by adding active PIN diode (UM9415, Microsemi Corp., Irvine, Calif.) detuning circuits to each drive rod which were controlled using DC bias from the MR scanner board (see FIGS. 9a-b). Additionally, fast switching diode controlled passive detuning circuits were added to other rods (1N6638U, Microsemi Corp., Irvine, Calif.). Isolation provided by diode detuning was characterized using an $S_{21}$ measurement between two small probes (2 cm diameter) lightly coupled to the coil in receive mode (diodes reverse biased) and transmit mode (diodes forward biased to deactivate the coil). Detuning of the i and q channels were separately characterized by orientating the small probes within the given birdcage such that they were parallel to one channel but orthogonal to the other.

To evaluate coil performance, SNR was measured on phantom images acquired using the birdcage array with each of the eight birdcage channels individually fed to standard preamplifiers on our 1.5 T system (Excite, GE Medical Systems, Waukesha, Wis.). Birdcage SNR was compared to that of four commercially available coils: 1) four-element long bone array (model 544GE-64, Medical Advances, Milwaukee, Wis.), 2) 12-element body array (model 165142, USA Instruments, Aurora, Ohio), 3) standard quadrature head coil with 28 cm diameter (GE Medical Systems) and, 4) standard body coil with 60 cm diameter (GE Medical Systems). For each coil, an axial slice was acquired at the S/I center of the phantom. SNR profiles in the anterior/posterior (A/P) direction were determined to highlight the contrasting birdcage and surface array performance. To simplify the results, a single profile for each coil was created by averaging the individual profiles from the left and right phantoms. Images were acquired using a fast gradient echo sequence with 5.1 ms echo time, 51 ms repetition time, 60° flip angle, 256×256 matrix, 48 cm FOV, 5 mm thickness, and 16-kHz receiver bandwidth. Noise was equal to the standard deviation of the pixel intensity within a large ROI in air space outside the phantom.

Ten angiographic examinations were performed on volunteers, who showed no signs of peripheral disease. The studies were approved by the local institutional review board, and written informed consent was obtained from each volunteer. Three imaging methods were applied during separate sessions: 1) Time-resolved 2D projection MRA of the thighs was performed on two volunteers, 2) a three-station bolus chase was performed on one volunteer, and 3) a four-station bolus chase was performed on seven volunteers. In each experiment, a time-of-flight sequence was used to localize the vasculature. A multiphase 2D fast-gradient echo acquisition similar to that described in Wang Y, et al., "Dynamic MR digital subtraction angiography using contrast enhancement, fast data acquisition, and complex subtraction," Magn Res Med 1996; 36(4):551-556 was used for the time-resolved 2D projection MRA acquisition. Images were acquired approximately every 2 seconds for 120 seconds. Images acquired prior to contrast arrival were visually identified and used as mask images from which subsequent contrast-enhanced images were subtracted. Complex subtraction was performed on the raw k-space data before Fourier transformation. The three-station bolus chase was performed using a 3D spoiled gradient echo sequence for acquisition in the coronal plane. Mask data were obtained at each station prior to Gd injection. The body coil was used for signal reception in the abdomen/pelvis, the large birdcage set for the thigh station, and the small birdcage set for the calf station. Contrast-enhanced data was then acquired by repeating the imaging routine following Gd injection. Final images were formed by subtracting mask data sets from corresponding contrast enhanced data sets. Table movements were performed automatically using standard software ($\approx$6 seconds to step between stations). To reduce venous contamination, all bolus chase images were acquired with thigh compression applied bilaterally at 50 mmHg using blood pressure cuffs.

A four station bolus chase protocol was devised to acquire MRA images from the trunk to the feet. To this end, the birdcage array was turned around such that the small birdcage set was superior to the large birdcage set. Here, the body coil was used for signal reception in the abdomen/pelvis and thigh stations, the small birdcage set for the calf station, and the large birdcage set for the foot station. We found that by imaging the feet prior to the calves, venous enhancement was reduced in the feet without compromising scan time in the other stations. Thus, the stations were ordered as follows: 1) abdomen/pelvis, 2) thighs, 3) feet, and 4) calves. Again, mask and contrast-enhanced data were acquired in order to utilize complex subtraction to highlight the vasculature.

The network analyzer was connected to both drive points to acquire the impedance spectra of a small birdcage in isolation ($Z_{11}$, $Z_{22}$ measurements). The spectra had a single, sharp resonant frequency peak at 63.87 MHz (FIG. 10a). The introduction of a neighboring birdcage caused the resonance peaks to split, as indicated by the simultaneous four port measurement ($Z_{11}, \ldots, Z_{44}$) shown in FIG. 10b. The $q_{left}$ channel split by about ±1.1 MHz, while the $i_{left}$ channel split asymmetrically by approximately −0.8 MHz and +2.2 MHz, indicating that the i channels exhibited stronger coupling compared to the q channels. Shared capacitors reduced magnetic coupling and the resonant frequency of all channels were restored to approximately 63.87 MHz (FIG. 10c).

TABLE 1

Birdcage array transmission coefficient ($S_{21}$) measurements.

| Channels | Small birdcage set $S_{21}$ (dB) | | Large birdcage set $S_{21}$ (dB) | |
| --- | --- | --- | --- | --- |
| | No decoupling | With decoupling | No decoupling | With decoupling |
| $i_{left}$, $q_{left}$ | −23 | −39 | −18 | −34 |
| $i_{right}$, $q_{right}$ | −19 | −44 | −19 | −35 |
| $i_{left}$, $i_{right}$ | −6.3 | −20 | −4.6 | −22 |
| $q_{left}$, $q_{right}$ | −5.5 | −31 | −1.8 | −20 |
| $i_{left}$, $q_{right}$ | −24 | −17 | −19 | −15 |
| $i_{right}$, $q_{left}$ | −18 | −16 | −17 | −15 |

Table 1 lists $S_{21}$ measurements taken on the unloaded birdcages. Coupling between channels addressed directly by a shared capacitor ($i_{left}$-$i_{right}$, $q_{left}$-$q_{right}$) was less than −20 dB. Greatest isolation was achieved between orthogonal channels within the same coil ($i_{left}$-$q_{left}$, $i_{right}$-$q_{right}$) which was controlled by adjusting the capacitance in the balancing rods as is done in conventional birdcage coils. Note that the shared electrical paths between $i_{left}$ & $i_{right}$ and between $q_{left}$ & $q_{right}$ were unequal. This required tweaking one linear channel within a given birdcage more than the other to recover quadrature isolation. Correspondingly, shared capacitors improved isolation between co-linear channels in adjacent birdcages ($i_{left}$-$i_{right}$, $q_{left}$-$q_{right}$), while isolation between non-colinear channels ($i_{left}$-$q_{right}$, $i_{right}$-$q_{left}$) was slightly worsened. However, due to their orthogonal orientation, these non-colinear channels were still reasonably isolated by about 15 dB without the use of any decoupling circuitry. With human leg loading, coupling was less than −20 dB for all channel combinations except the non-colinear channels. The non-colinear channels were isolated by 14 dB (large birdcages) and 17 dB (small birdcages).

FIG. 11a shows a phantom image obtained using one small birdcage coil with two phantoms. The ratio of signal received from the right phantom to that from the left phantom was 7.2:1 (4.8:1 for one large birdcage, images not shown). This figure was reduced to 1.2:1 when a second small birdcage was introduced without decoupling (1.3:1 for the coupled large birdcages). This indicates substantial signal and noise leakage between coils (FIGS. 11b-c). The decoupling capacitors did not entirely eliminate signal from the contralateral phantom, but it was reduced to 6.5:1 (3.9:1 for the large birdcages), which is comparable to that obtained with one coil in isolation (FIGS. 11d-e). As a result of reduced coil spacing and increased size, the large birdcage set experienced greater signal coupling than the small birdcage set.

Figure 12:
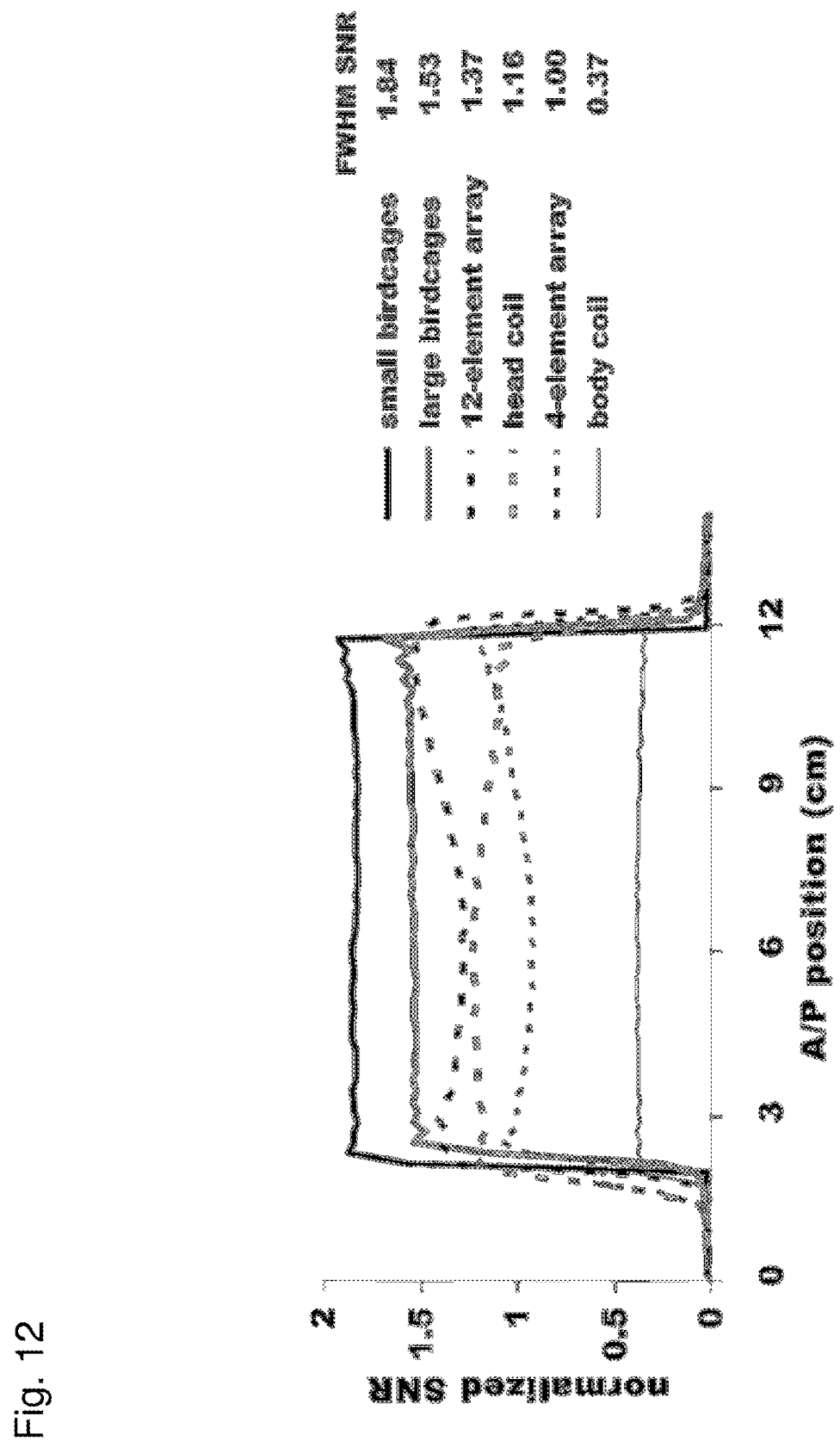
FIG. 12 illustrates the SNR profiles along the anterior-posterior direction using six different coil arrays. Full width at half maximum (FWHM) SNR is given in the legend.

Diode detuning provided 23.5 dB to 25.6 dB isolation between transmit and receive modes of the large birdcages and between 25.2 dB and 28.6 dB isolation for the small birdcages. SNR profiles along the AP direction are given in FIG. 12. The full width at half maximum (FWHM) SNR listed in the legend show the small and large birdcage sets attained 58% and 32% improvement over the standard head coil, respectively. Similar gains were achieved over the four and 12 element surface arrays.

Figure 13:
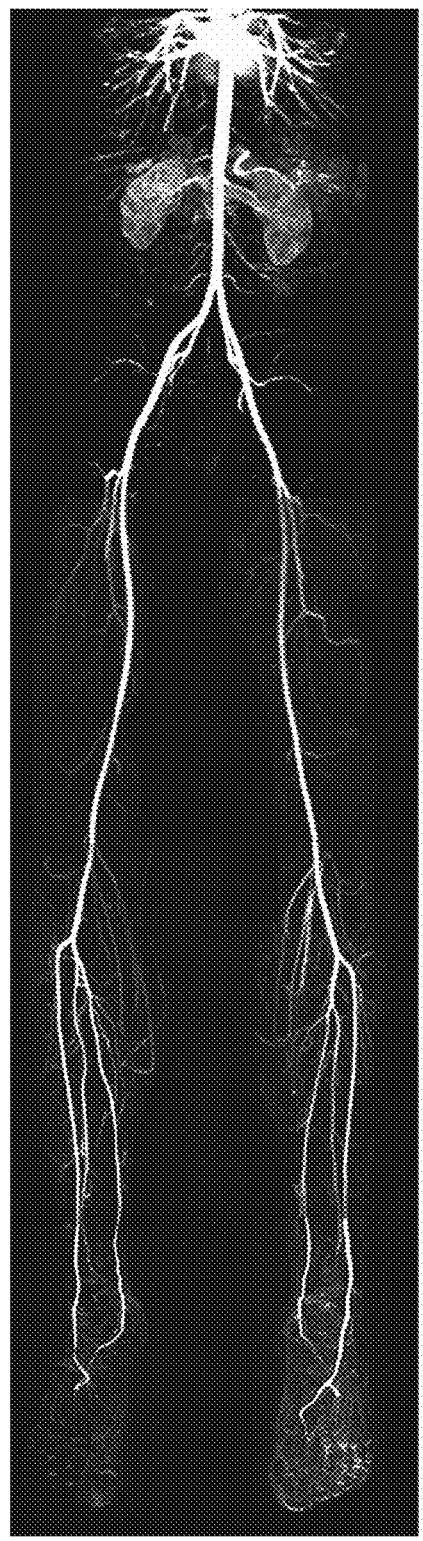
FIG. 13 illustrates a four-station 3D bolus chase MRA using the volume coils of FIG. 8 in accordance with an exemplary embodiment of the invention.

A four-station bolus chase image is shown in FIG. 13. A multitude of smaller branches can be seen, especially in the calf station. Although the large birdcage set was not optimized for feet loading, the dorsal and posterior tibial arteries can be visualized.

Birdcage coils are ideal for lower extremity angiography because their signal homogeneity simplifies post-processing by volume rendering MIP techniques. In addition, birdcage coils provide good SNR in the center of the coils, where lower extremity arteries tend to be located. However, difficulties with coupling have led to the use of the birdcage head coil to encircle both feet and calves for most peripheral MRA birdcage studies (Zhu H, Buck D G, Zhang Z, Zhang H, Wang P, Stenger V A, Prince M R, Wang Y, "High temporal and spatial resolution 4D MRA using spiral data sampling and sliding window reconstruction," Magn Reson Med 2004; 52(1):14-18). Here, this coupling problem was solved using shared capacitors among parallel modes in the left and right birdcages instead of shielding and natural decoupling among orthogonal modes, which allowed multiple smaller birdcages to cover each leg individually.

Measurements showed that the birdcage array achieved improved SNR compared to the standard quadrature head coil. These gains can be attributed to a reduced coil radius (to improve sensitivity) as well reduced noise detection. Specifically, noise was reduced because the head coil was burdened by the resistive losses from two legs or phantoms whereas each birdcage array element was burdened by one. The birdcage array also provided improved SNR compared to commercially available four and 12 element surface coil arrays. Improvement over the surface arrays was partially due to the fact that their geometry imposes limitations on their sensitivity, for the most part, to the vertical $B_1$ field, whereas the birdcages were sensitive to both vertical and horizontal fields.

Conventionally, angiographic examination of the abdomen/pelvis and lower limbs is accomplished using a three-station bolus chase technique. Imaging commences in the abdomen/pelvis (station 1) immediately upon bolus arrival in the aorta. Next, the table is repositioned and imaging is performed on the thighs (station 2) and subsequently the calves (station 3) as quickly as possible to keep up with the bolus as it travels down the legs. In conflict with the time restraint imposed by the arterial contrast window, sufficient spatial resolution is required to visualize smaller arteries in the lower extremities, placing additional emphasis on coil performance. The three-station bolus chase image indicates adequate SNR was provided by the birdcage array to resolve a number of smaller vessels in the thighs and calves.

To delineate the pedal arteries, a four-station protocol was created in which the small birdcage set covered the calves and the large set covered the feet. Originally, the four stations were ordered sequentially; 1) abdomen/pelvis, 2) thighs, 3) calves, and 4) feet. With this protocol, feet imaging began about 84 seconds after bolus arrival in the aorta (including time for table movement). However, venous enhancement in the feet indicated that this delay was too long. To image the pedal arteries sooner, the order of the final two stations was reversed; 1) abdomen/pelvis, 2) thighs, 3) feet, and 4) calves. This allowed pedal imaging to begin about 43 seconds after bolus arrival in the aorta, virtually eliminating pedal venous enhancement (FIG. 13). Given that the veins in the calves fill later than those in the feet, we were able to scan the feet and then retreat back to the calves in time to spend 38 seconds collecting an uncontaminated calf image with 0.8×1.6×4 mm³ resolution Parallel imaging was performed by taking advantage of the distinct spatial sensitivity in the L/R direction. The array performed well for parallel reconstructions of two-fold undersampled data. However, it is limited to a reduction factor of two. This is a disadvantage of the birdcage array, as greater reduction factors have been demonstrated using surface arrays.

An additional limitation of the birdcage array is that its closed geometry restricts the size of eligible patients. This can be particularly limiting for thigh imaging, as thigh diameters tend to have substantial variation among the patient population. In contrast, typical peripheral surface coils utilize an open geometry design which eliminates this problem.

Long wires were required to connect the decoupling capacitors, particularly in the case of the q channels. Effects of the inductance added by the long wire were minimized by distributed capacitors along the decoupling rods and by the decoupling capacitor itself. The influence of this inductance on coil performance was not specifically tested, but Q measurements were similar with and without decoupling circuitry, suggesting it was not deleterious to coil function. However, this design may be more troublesome at higher field strength, necessitating additional distributed capacitors.

Phantom images acquired using the birdcage coils illustrate inhomogeneous SNR profiles, as the medial sensitivity is greater than that at the peripheries (FIGS. 11a-e). This shading artifact may be a result of asymmetries introduced by the decoupling circuitry. However, images acquired using the body coil for signal excitation and reception exhibit similar shading, suggesting it may also be a consequence of inhomogeneous RF excitation accentuated by operating away from the magnet isocenter (FIG. 11f).

In the MRA experiments, the body coil was used for signal reception in the abdomen/pelvis station. Using a switching device to control which coils are active, an abdomen surface coil could be implemented in conjunction with the distal birdcage coils. This may warrant further consideration and allow similar quality with a lower dose of gadolinium.

In conclusion, the practical value of a birdcage array was demonstrated. Due to their homogenous sensitivity, good SNR, and cylindrical geometry, birdcages are a natural choice for lower extremity imaging. Shared capacitors alleviated coupling between coils, allowing a single birdcage to encompass each leg individually and providing a novel approach for peripheral imaging.

What is claimed is:

1. A device configured for detecting magnetic resonance imaging radiofrequency signals simultaneously and independently from right and left legs of a patient, comprising:
   a first left leg quadrature volume coil having a first mode and a second mode;
   a first right leg quadrature volume coil having a third mode and a fourth mode;
   no conductive shielding surrounding or between the left leg quadrature volume coil and the right leg quadrature volume coil;
   a fixed orientation of the first right leg quadrature volume coil with respect to the first left leg quadrature volume coil with:
      the first mode being perpendicular to the second mode;
      the third mode being perpendicular to the fourth mode;
      the first mode being parallel to the third mode; and
      the second mode being parallel to the fourth mode; and
   two adjustable shared reactive components which controllably decouple modes that are parallel between the first right leg quadrature volume coil and the first left leg quadrature volume coil, with the first and third modes physically and electrically connected to one another by one shared reactive component and the second and fourth modes physically and electrically connected to one another by the second shared reactive component;
   wherein the shared reactive components are adjusted to decouple from one another the modes that are parallel to one another.

2. The device according to claim 1, wherein the first right and left leg quadrature volume coils are birdcage coils.

3. The device according to claim 1, wherein at least one of the adjustable shared reactive components comprises a capacitor.

4. The device according to claim 1, wherein at least one of the adjustable shared reactive components comprises an inductor.

5. The device according to claim 1, wherein the first and third modes are sensitized to horizontal magnetizations and the second and fourth modes are sensitized to vertical magnetizations.

6. The device according to claim 1, comprising:
a second left leg quadrature volume coil inferior to the first left leg quadrature volume coil with a superior margin of second left leg quadrature volume coil overlapped with an inferior margin of the first left leg quadrature volume coil in order to decouple the first and second left leg quadrature volume coils from one another; and
a second right leg quadrature volume coil inferior to the first right leg quadrature volume coil with a superior margin of second right leg quadrature volume coil overlapped with an inferior margin of the first right leg quadrature volume coil in order to decouple the first and second right leg quadrature volume coils from one another.

7. A The device according to claim 6, wherein:
the first right and left leg quadrature volume coils are each sized and shaped in order to fit around a thigh; and
further comprising:
a left calf quadrature volume coil and a right calf quadrature volume coil, each sized and shaped in order to fit around a calf; and
a left foot quadrature volume coil and a right foot quadrature volume coil, each sized and shaped in order to fit around a foot.

8. The device according to claim 7, wherein the left and right foot quadrature volume coils are end capped.

9. The device according to claim 7, wherein each foot coil has an opening configured for toes.

10. A device configured for detecting magnetic resonance imaging radiofrequency signals simultaneously from right and left legs of a patient, comprising:
two cylindrical spaces sized and shaped in order to fit the right and left legs, the cylindrical spaces formed by at least:
a first medial surface coil array interposed between the two legs, the medial array comprising first and second medial coils that are oriented orthogonal to one another, which permits the medial coils of the first medial surface coil array to be thereby decoupled from one another;
a first lateral surface coil array comprising at least two lateral coils, one sized and shaped for positioning on the outside of the right leg and one sized and shaped for positioning on the outside of the left leg, with the lateral coils being separated in order to decouple the lateral coils from one another; and
no conductive shielding surrounding or between the first medical coil, the second medical coil, the first lateral coil, and the second lateral coil;
wherein the lateral coils of the first lateral surface coil array are positioned in order to partially overlap the medial coils of the first medial surface coil array and in order to minimize coupling between each lateral coil and both medial coils that comprise the first medial surface coil array; and
wherein each medial coil of the first medial surface coil array forms at least a part of both the cylindrical space for the right leg and the cylindrical space for the left leg.

11. The device according to claim 10, wherein the first medial surface coil array and the first lateral surface coil array are decoupled by at least one shared reactive component.

12. The device according to claim 11, wherein the shared reactive component comprises a capacitor.

13. The device according to claim 11, wherein the shared reactive component comprises an inductor.

14. The device according to claim 10, wherein:
the first medial coil of the medial coil array forms a top of the cylindrical space configured for the left leg and a bottom of the cylindrical space configured for the right leg; and
the second medial coil of the medial coil array forms a bottom of the cylindrical space configured for the left leg and a top of the cylindrical space configured for the right leg.

15. The device according to claim 10, further comprising:
a second medial surface coil array inferior to the first medial surface coil array with a superior margin of the second medial surface coil array overlapped with an inferior portion of the first medial surface coil array in order to decouple the first and second medial surface coil arrays from one another; and
a second lateral surface coil array inferior to the first lateral surface coil array with a superior margin of the second lateral surface coil array overlapped with an inferior portion of the first lateral surface coil array in order to decouple the first and second lateral surface coil arrays from one another.

16. The device according to claim 15, wherein
the first lateral and medial surface coil arrays are sized and shaped in order to fit around the patient's thighs; and
further comprising:
a calf medial surface coil array and a calf lateral surface coil array sized and shaped in order to fit around the patient's calves; and
a foot medial surface coil array and a foot lateral surface coil array sized and shaped in order to fit around the patient's feet.

17. The device according to claim 16, wherein the foot medial coil array and the foot lateral coil array have openings configured for toes.

18. The device according to claim 10, wherein the orthogonal elements of the first medial surface coil array are respectively sensitized to magnetization from both legs at 45 and 135 degrees away from a horizontal direction.

19. The device according to claim 10, wherein the first lateral surface coil array is sensitized to horizontal magnetization from both legs.

20. A method for imaging arteries in both right and left lower extremities simultaneously and independently by MRI comprising:
placing a first left leg quadrature volume coil having a first mode and a second mode on a left leg and placing a first right leg quadrature volume coil having a third mode and fourth mode on a right leg;
having no conductive shielding surrounding or between the volume coils;
fixing the orientation of the first right leg quadrature volume coil with respect to the first left leg quadrature volume coil wherein:
the first mode is perpendicular to the second mode;
the third mode is perpendicular to the fourth mode;
the first mode is parallel to the third mode; and
the second mode is parallel to the fourth mode; and
controllably decoupling parallel modes by using a first adjustable shared reactive component that physically and electrically interconnects the first and third modes with one another and a second adjustable shared reactive component that physically and electrically interconnects the second and fourth modes with one another.

21. The method according to claim 20 wherein the first right and left leg quadrature volume coils are birdcage coils.

22. The method according to claim 20, wherein at least one of the adjustable shared reactive components comprises a capacitor.

23. The method according to claim 20, wherein at least one of the adjustable shared reactive components comprises an inductor.

24. The method according to claim 20, wherein the first and third modes are sensitized to horizontal magnetizations and the second and fourth modes are sensitized to vertical magnetizations.

25. The method according to claim 20, further comprising:
placing a second left leg quadrature volume coil on the left leg inferior to the first left leg quadrature volume coil with a superior margin of second left leg quadrature volume coil overlapped with an inferior margin of the first left leg quadrature volume coil in order to decouple the first and second left leg quadrature volume coils from one another; and
placing a second right leg quadrature volume coil on the right leg inferior to the first right leg quadrature volume coil with a superior margin of second right leg quadrature volume coil overlapped with an inferior margin of the first right leg quadrature volume coil in order to decouple the first and second right leg quadrature volume coils from one another.

26. The method according to claim 25, wherein:
the first right and left leg quadrature volume coils are each optimized in order to fit around a thigh; and
further comprising:
placing a left calf quadrature volume coil on a left calf, the left calf quadrature volume coil sized and shaped in order to fit around a calf; and
placing a right calf quadrature volume coil on a right calf, the right calf quadrature volume coil sized and shaped in order to fit around a calf; and
placing a left foot quadrature volume coil on a left foot, the left foot quadrature volume coil sized and shaped in order to fit around a foot; and
placing a right foot quadrature volume coil on a right foot, the right foot quadrature volume coil sized and shaped in order to fit around a foot.

27. The method according to claim 26, wherein the left and right foot quadrature volume coils are end capped.

28. The method according to claim 26, wherein the left and right foot quadrature volume coils have an opening configured for toes.

* * * * *